United States Patent [19]

Mallucci et al.

[11] Patent Number: 6,127,169
[45] Date of Patent: Oct. 3, 2000

[54] NON-AGGLUTINATING β-GALACTOSIDE BINDING PROTEIN AND ITS ENCODING NUCLEIC ACID

[76] Inventors: Livio Mallucci, 124 Sunningfields Road, London NW4 4RE; Valerie Wells, 46 Constantine Road, London NW3 2NE, both of United Kingdom

[21] Appl. No.: 08/050,259

[22] PCT Filed: Oct. 30, 1991

[86] PCT No.: PCT/GB91/01898

§ 371 Date: Apr. 30, 1993

§ 102(e) Date: Apr. 30, 1993

[87] PCT Pub. No.: WO92/07938

PCT Pub. Date: May 14, 1992

[30] Foreign Application Priority Data

Nov. 2, 1990 [GB] United Kingdom .................. 9023907

[51] Int. Cl.$^7$ .............................. C12N 1/00; C12N 15/63
[52] U.S. Cl. ..................... 435/320.1; 435/69.1; 435/243; 435/325; 514/2; 530/350; 536/23.5
[58] Field of Search ...................... 530/350, 395; 514/2; 435/243, 320.1, 325, 69.1, 252.3, 254.11; 536/23.5

[56] References Cited

FOREIGN PATENT DOCUMENTS

| 0 260497 | 3/1988 | European Pat. Off. . |
|---|---|---|
| WO 01519 | 2/1989 | WIPO . |

OTHER PUBLICATIONS

Kajikawa, T., et al., "Release of Cytotoxin By Macrophages on Treatment with Human Placenta Lectin", *Life Sciences*, 39:1177–1181 (1986).

Hynes, M. A., et al., "Selective Expression of an Endogenous Lactose–Binding Lectin Gene in Subsets of Central and Peripheral Neurons", *The Journal of Neuroscience*, 10(3) :1004–1013 (1990).

Kenichi, K., "Human Placenta– or Umbilical Cord–Derived Lectin", 1–110698(A), 100 C 622.

Clerch, L. B., et al., "Sequence of a Full–Length cDNA for Rat Lung β–Galactoside–Binding Protein: Primary and Secondary Structure of the Lectin", *Biochemistry*, 27:692–699 (1988).

Couraud, P–O., et al., "Molecular Cloning, Characterization, and Expression of a Human 14–kDa Lectin", *The Journal of Biological Chemistry*, 264(2) :1310–1316 (1989).

Greene, W. C., et al., "Soluble Suppressor Supernatants Elaborated by Concanavalin A–Activated Human Mononuclear Cells", *The Journal of Immunology*, 126(3) : 1185–1191 (1981).

Chany–Fournier, F., et al., "Action inhibitrice sur le developpement de la tumeur 180/TG de Crocker de l'antagoniste tissuelaire de l'interferon : lectine murine nouvellement reconnue", *C. R. Acad. Sc. Paris*, t.286:1550–1553 (1978).

Drickamer, K., et al., "Two Distinct Classes of Carbohydrate–recognition Domains in Animal Lectins", *The Journal of Biological Chemistry*, 263(20) :9557–9560 (1958).

Hirabayashi, J., et al., "Complete Amino Acid Sequence of a β–Galactoside–Binding Lectin from Human Placenta", *J. Biochem.*, 104:1–4 (1988).

Horabayashi, J., et al., "Cloning and nucleotide sequence of a full–length cDNA for human 14 kDa β–galactoside–binding lectin", *Biochimica et Biophysica Acta*, 1008:85–91 (1989).

Wells et al., Journal of Cellular Physiology, vol. 117, p. 148, 1983 .

Wilson et al., Biochem J., vol. 261, p. 847, 1989.

Sambrook et al., Molecular Cloning, A Laboratory Manual, vol. 2, Chp. 16, Cold Spring Harbor Lab., 1989.

Barondes, Science, 233, 1259–1264, 1984.

*Primary Examiner*—Sally P. Teng
*Attorney, Agent, or Firm*—Flehr Hohbach Test Albritton & Herbert LLP; David J. Brezner

[57] ABSTRACT

Non-agglutinating β-galactoside binding proteins (GBP), both the natural proteins and proteins produced by recombinant DNA technology, are provided for use as inhibitors and regulators of vertebrate cell growth and as anti-viral agents. Methods of producing the GBP's are also described. The GBP's show a powerful growth inhibitory effect against human cancer cells making them potentially useful therapeutic agents in the treatment of malignant disease and also show an inhibitory effect on viral replication making them potentially useful as anti-viral agents.

20 Claims, 19 Drawing Sheets

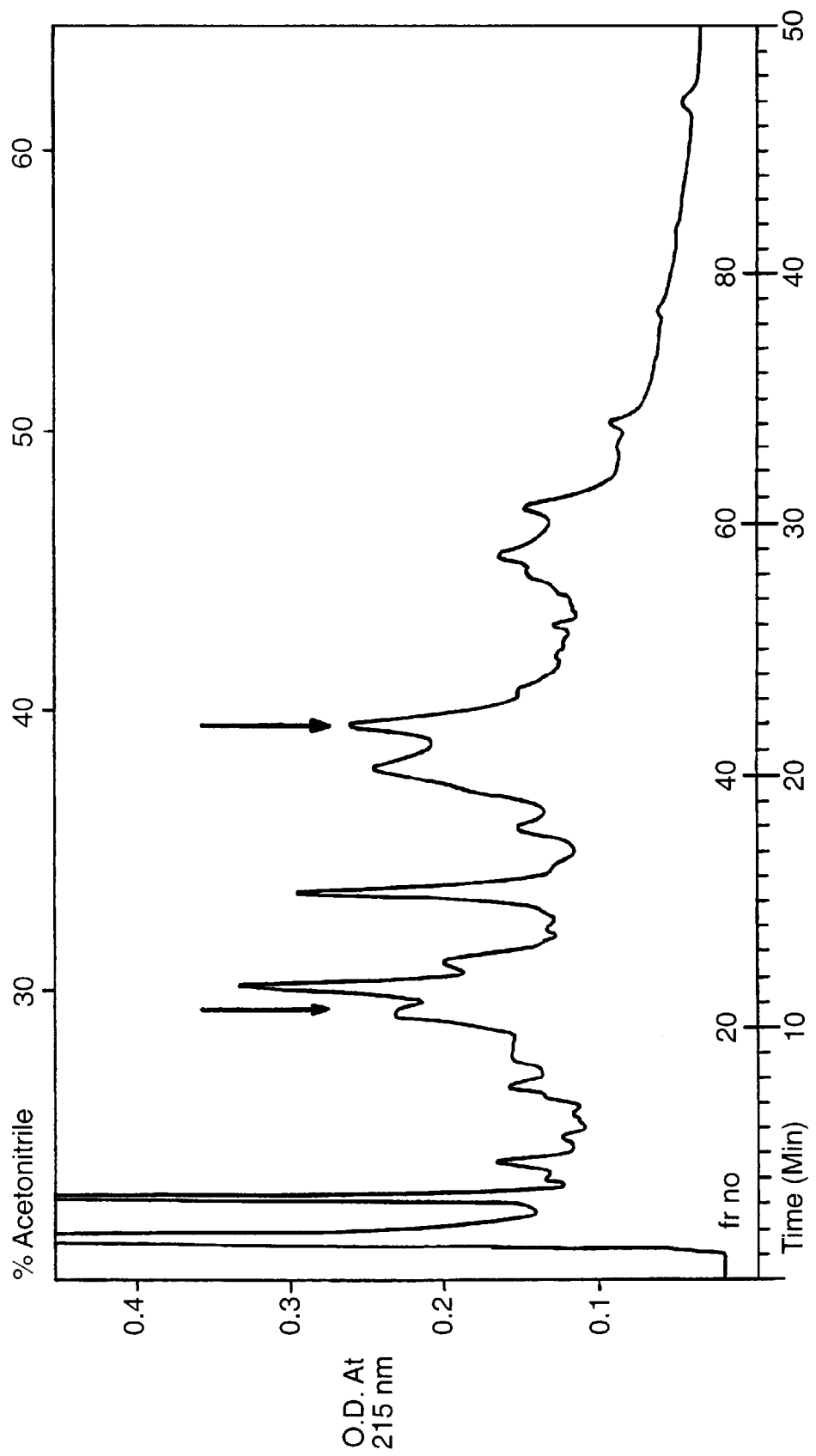

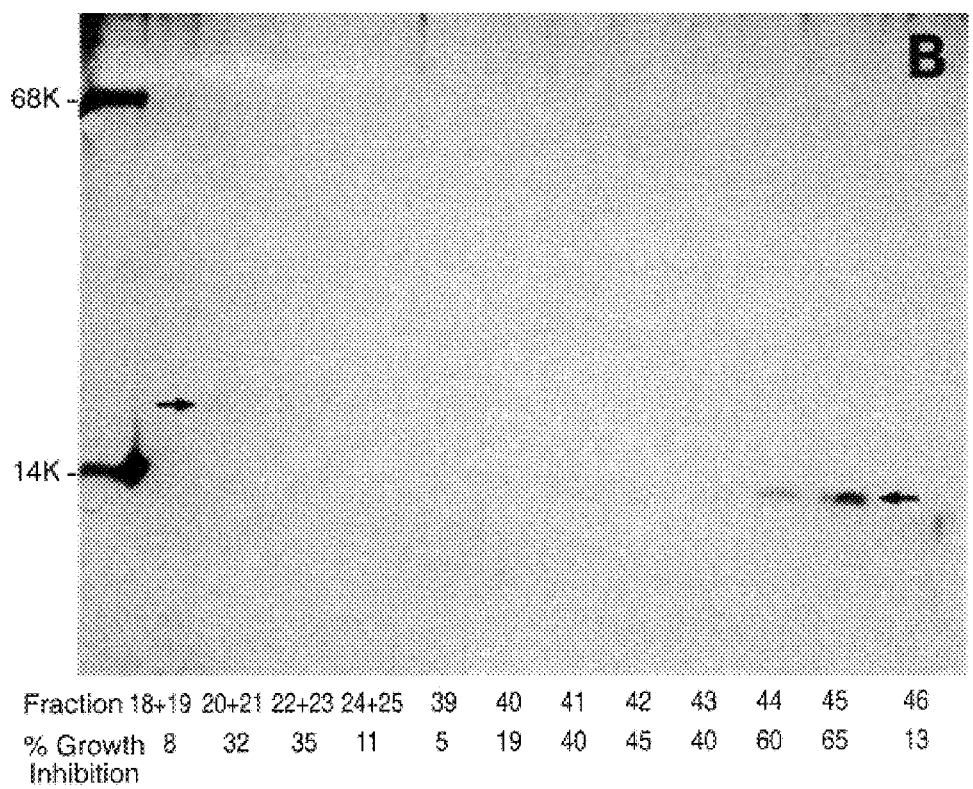
FIG._1B
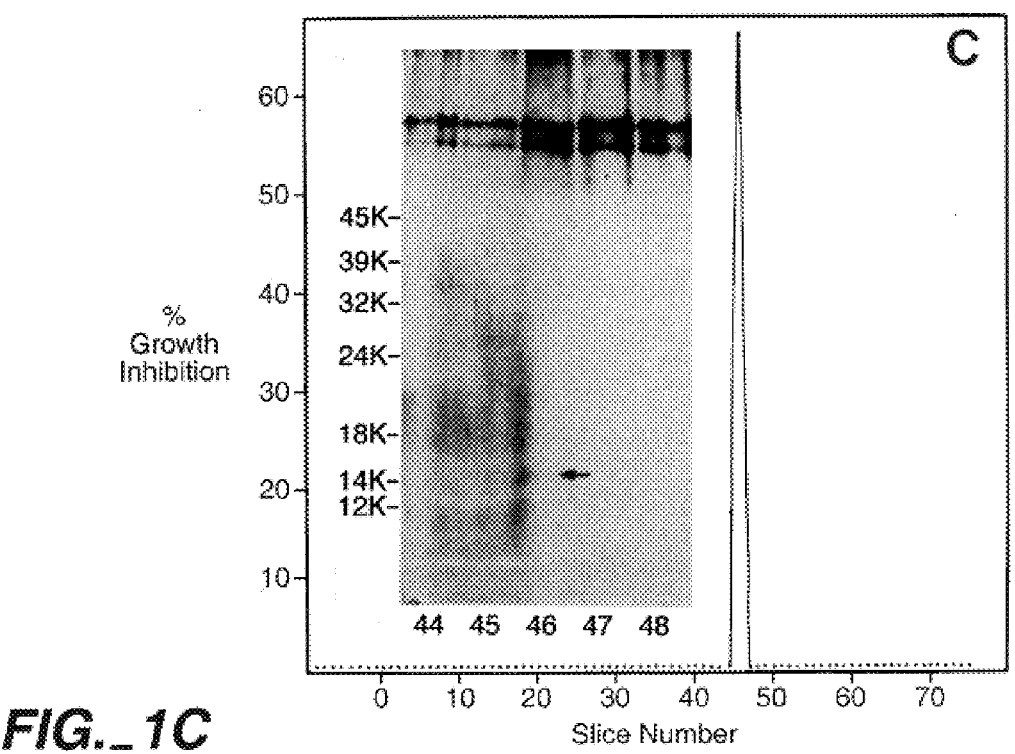
FIG._1C

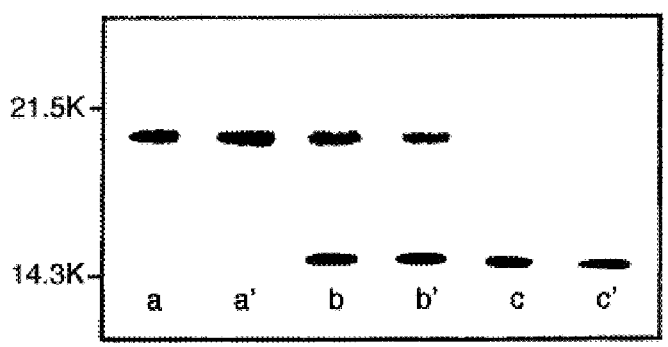
FIG._1Da
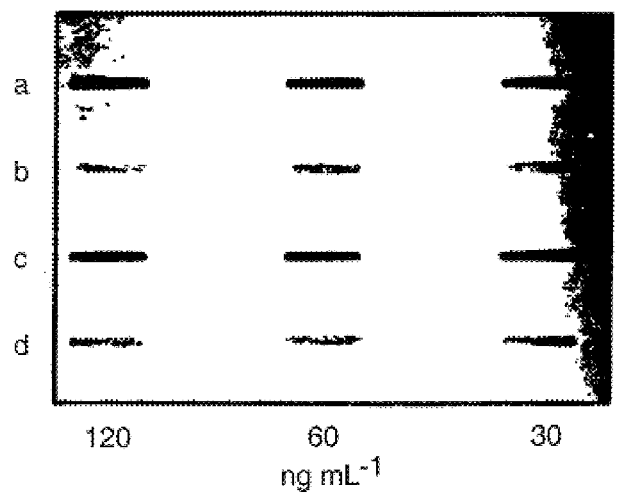
FIG._1Db
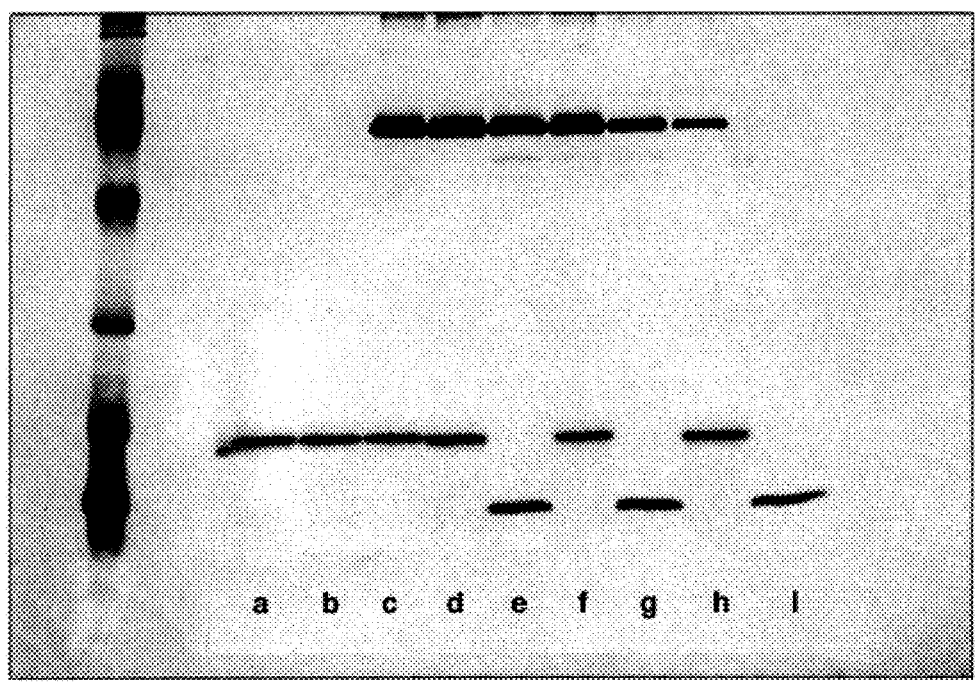
FIG._1E

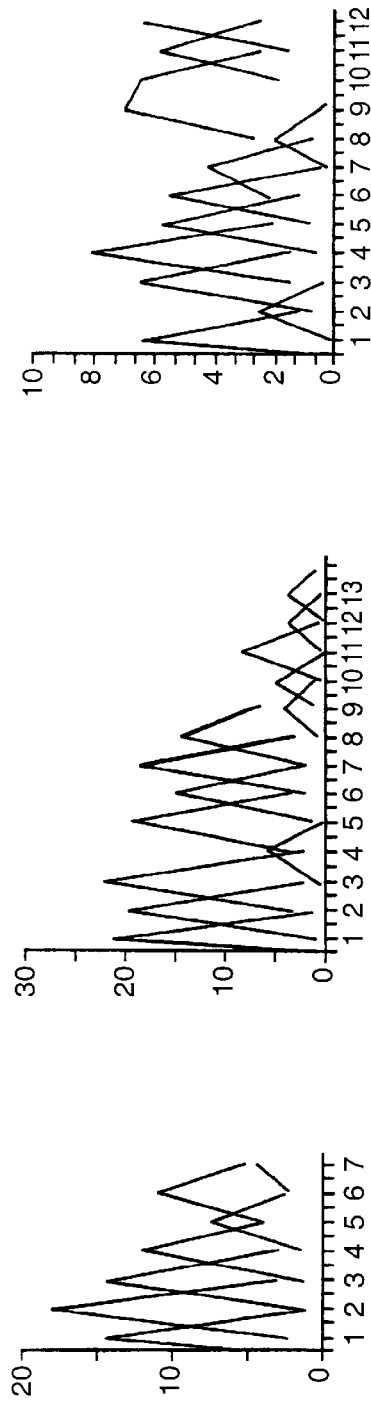
FIG._2A

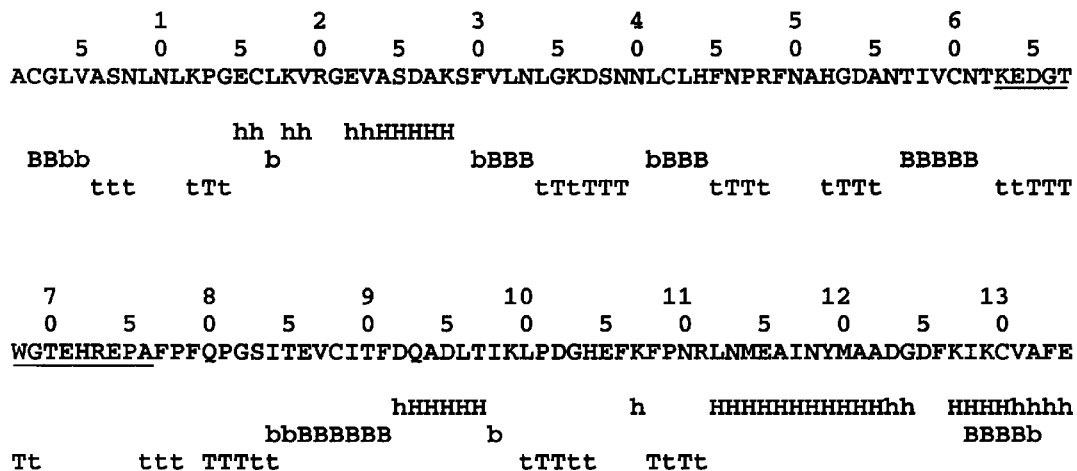
FIG._2Ba
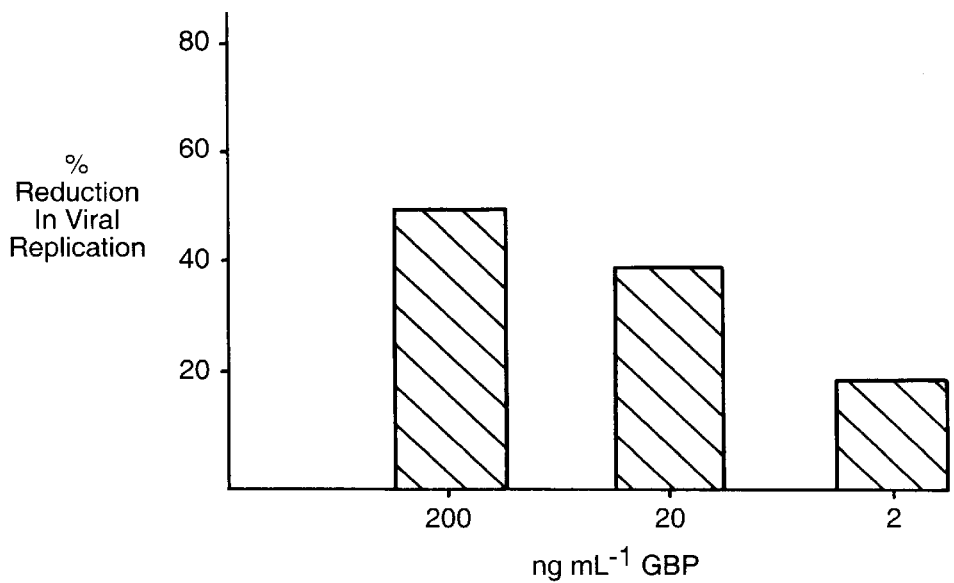
FIG._9

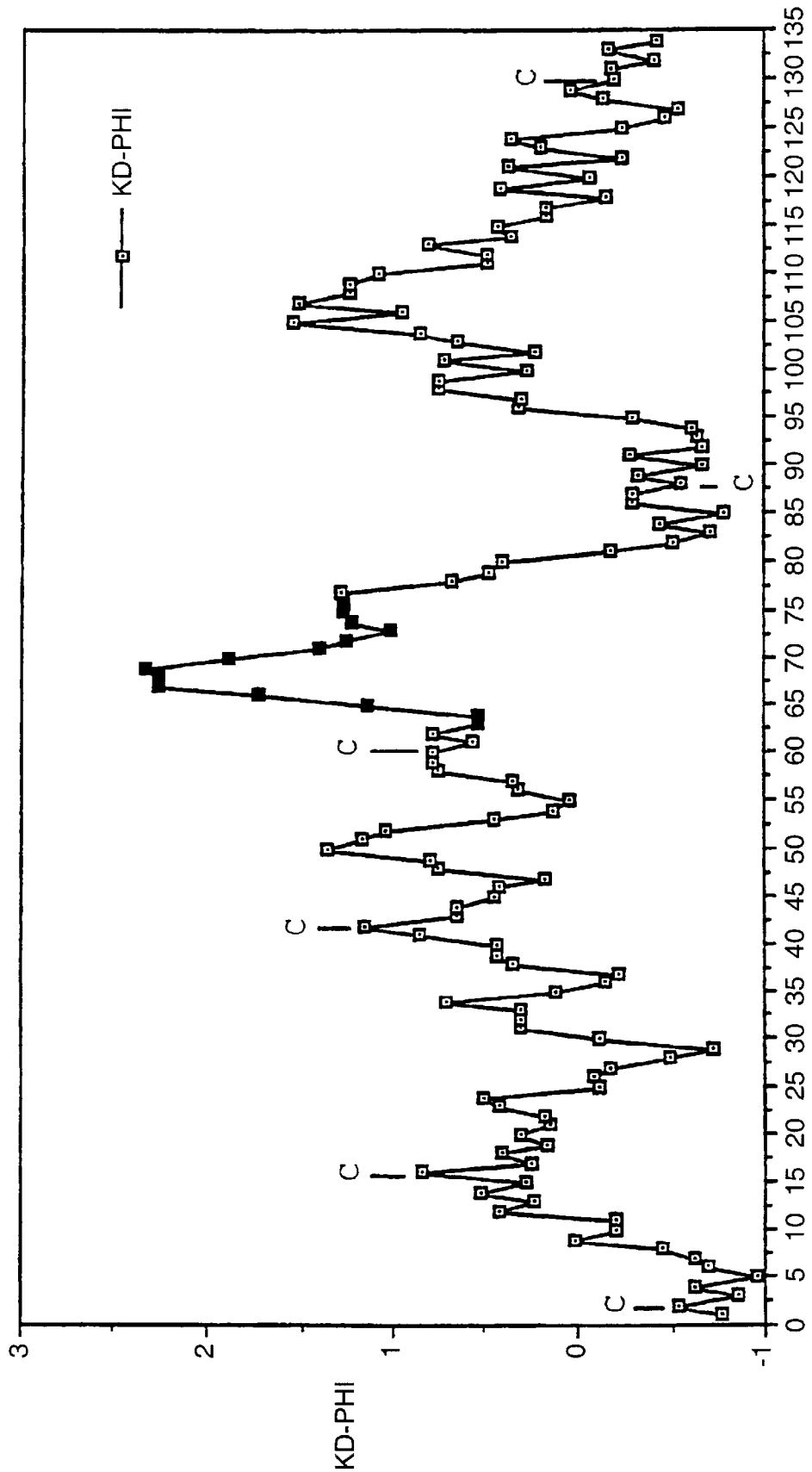
FIG._2Bb

```
 -19          5' - CTTCGCTTCAGCTTCAATC

+1  ATG CCC TGT GGT CTG GTC GCC AGC AAC CTG AAT CTC AAA CCT GGG GAA TGT CTC AAA GTT CGG GGA GAG GTG GCC
       M   P   C   G   L   V   A   S   N   L   N   L   K   P   G   E   C   L   K   V   R   G   E   V   A

+76  TCG GAC GCC AAG AGC TTT GTG CTG AAC CTG GGA AAA GAC AGC AAC AAC CTG TGC CTA CAC TTC AAT CCT CGC TTC
       S   D   A   K   S   F   V   L   N   L   G   K   D   S   N   N   L   C   L   H   F   N   P   R   F

+151  AAT GCC CAT GGA GAC GCC AAC ACC ATT GTG TGT AAC ACC AAG GAA GAT GGG AAC TGG GGA ACC GAA CAC CGG GAA
       N   A   H   G   D   A   N   T   I   V   C   N   T   K   E   D   G   T   W   G   T   E   H   R   E

+226  CCT GCC TCC CCT TTC CAG CCT TTC CAG CCT GGG AGC ATC ACA GAG GTG TGC ATC AAC TTT GAC CAG GCT GAC CTG ACC ATC AAG
       P   A   F   P   F   Q   P   F   Q   P   G   S   I   T   E   V   C   I   N   F   D   Q   A   D   L   T   I   K

+301  CTG CCA GAC GGA CAT GAA TTC AAG TTC CCA AAC CGC CTC AAC ATG GAG GCC ATC AAC TAC ATG GCG GCG GAT GGA
       L   P   D   G   H   E   F   K   F   P   N   R   L   N   M   E   A   I   N   Y   M   A   A   D   G

+376  GAC TTC AAG ATT AAG TGC GTG GCC TTT GAG TGAAGCCAGCCAGCCTGTAGCCCTCAATAAAAGGCAGCTGCCTCTGCTCCCCATAAAAA
       D   F   K   I   K   C   V   A   F   E

+465  AAAAAAAAAAAAA - 3'
```

*FIG._3A*

-45  5'- TGAGACAGCAGATATCAATACACTAACATCCTCCTGGACTCAATC

+1   ATG GCT TGT GGT CTG GTC GCC AGC AAC CTG AAT CTC AAA CCT GGA GAG TGC CTT CGA GTG CGA GGC GAG GTG GCT
     M   A   C   G   L   V   A   S   N   L   N   L   K   P   G   E   C   L   R   V   R   G   E   V   A

+76  CCT GAC GCT AAG AGC TTC GTG TTC AAC GAC AGC AAA GAC AGC AAG GAC AGC AAG GAC AGC AAC CTG CAC TTC AAC CCT CGC TTC
     P   D   A   K   S   F   V   F   N   D   S   K   D   S   N   L   H   F   N   P   R   F

+151 AAC GCC CAC GGC GAC GCC AAC ACC ATC GTG TGC AAC AGC AAG GAC GGC TGG GGG ACC CAG CAG CGG GAG
     N   A   H   G   D   A   N   T   I   V   C   N   S   K   D   G   W   G   T   Q   Q   R   E

+226 GCT GTC TTT CCC TTC CAG CCT GGA AGT GTT GCA GAG GTG TGC CTG AAC CGC CTG AAC CTG ACC AAC GTC AAG
     A   V   F   P   F   Q   P   G   S   V   A   E   V   C   L   N   R   L   N   L   T   V   K

+301 CTG CCA GAT GGA TAC GAA TTC AAG TTC TTC CCC AAC CGC CTG AAC CTG GAG GCC ATC AAC TAC ATG GCA GCT GAC GGT
     L   P   D   G   Y   E   F   K   F   F   P   N   R   L   N   L   E   A   I   N   Y   M   A   A   D   G

+376 GAC TTC AAG ATC AAA TGT GTG GCC TTT GAC TGAAAATCAGCCACGCCATGGCCCCCG -3'
     D   F   K   I   K   C   V   A   F   D

FIG._3B

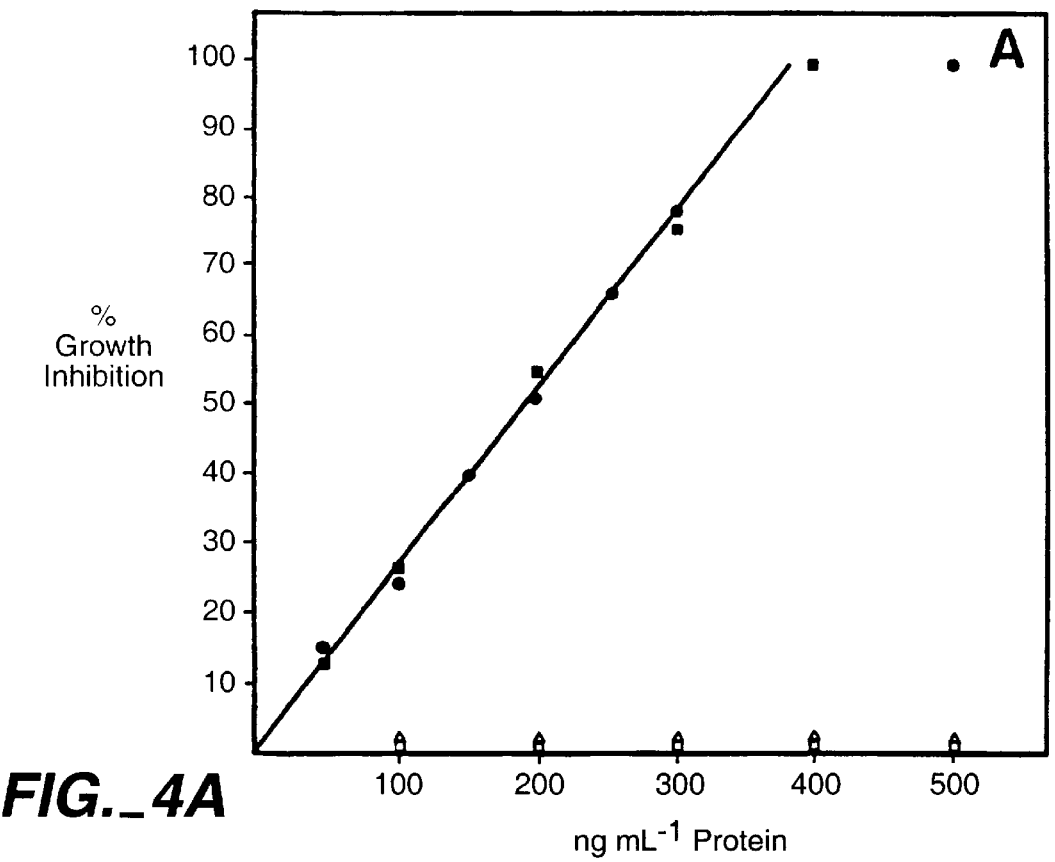
FIG._4A
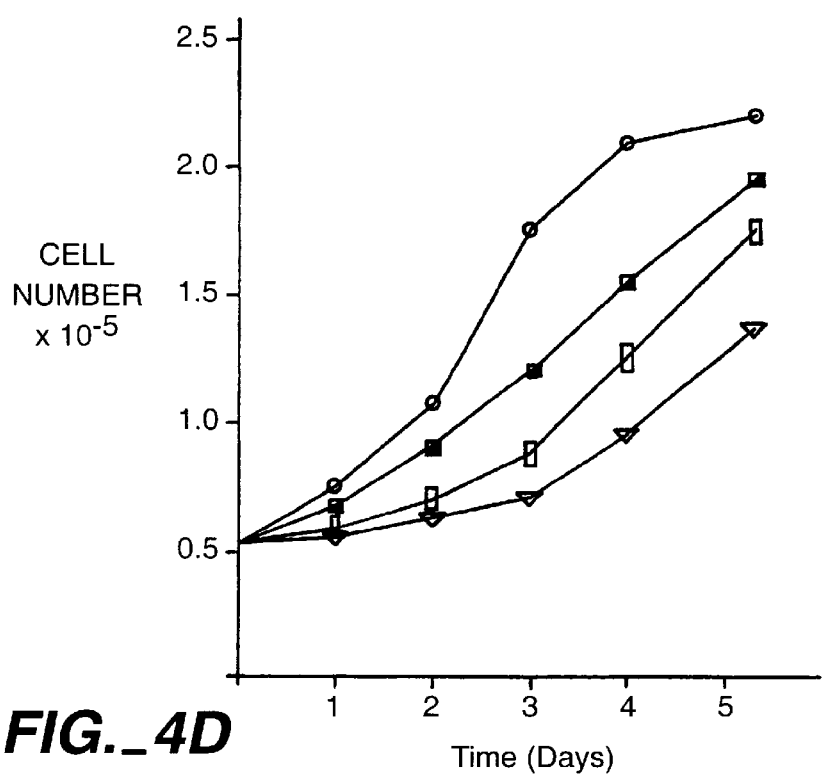
FIG._4D

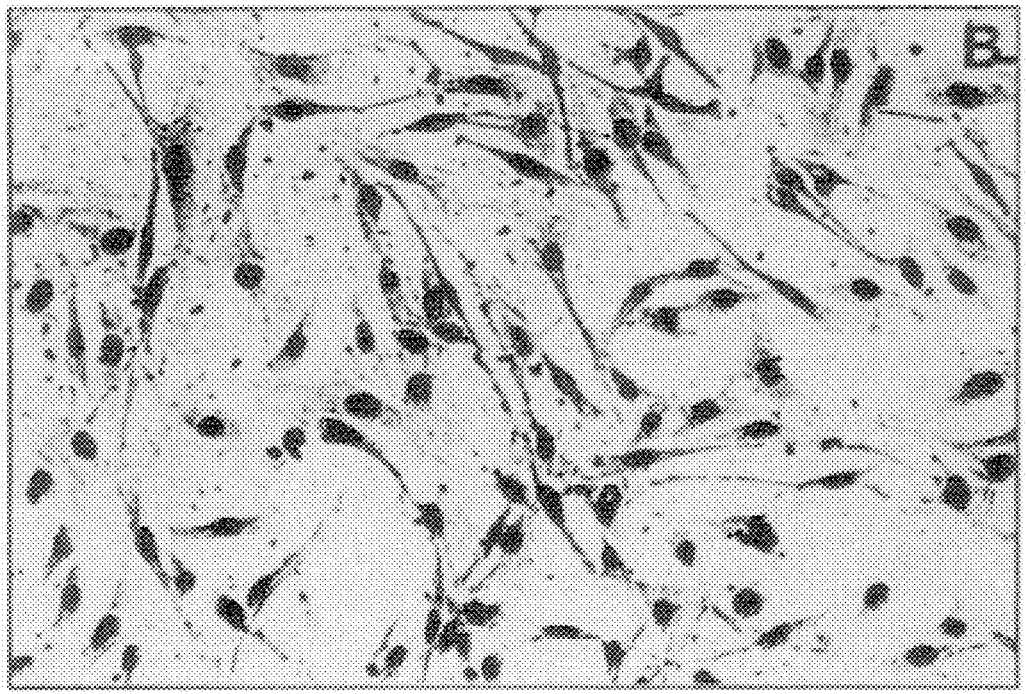
*FIG._4B*
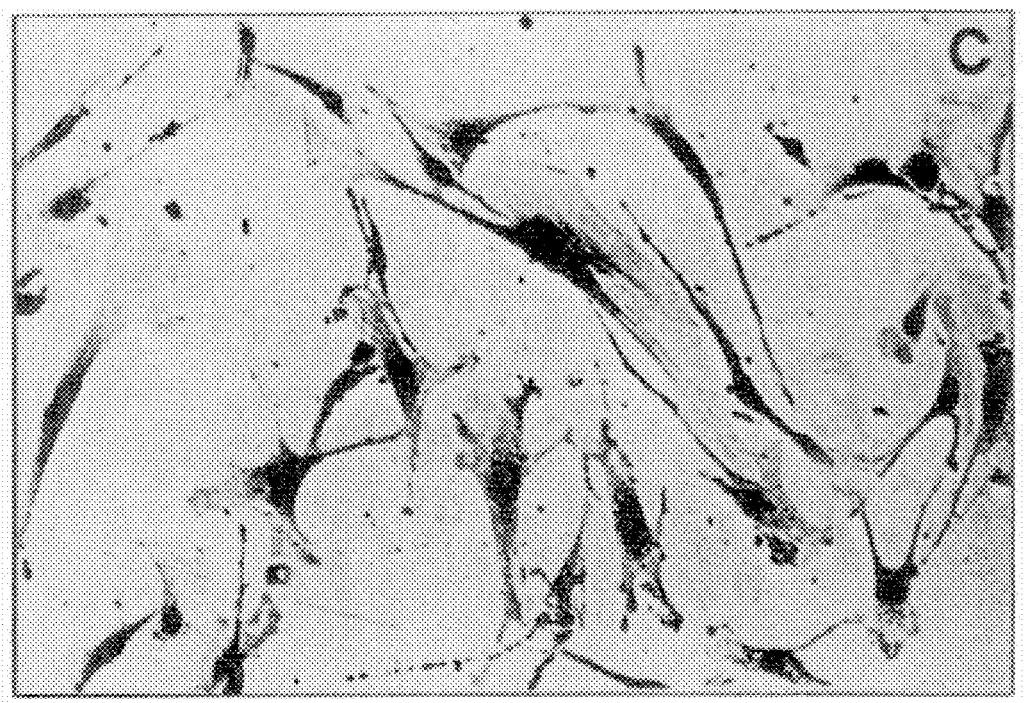
*FIG._4C*

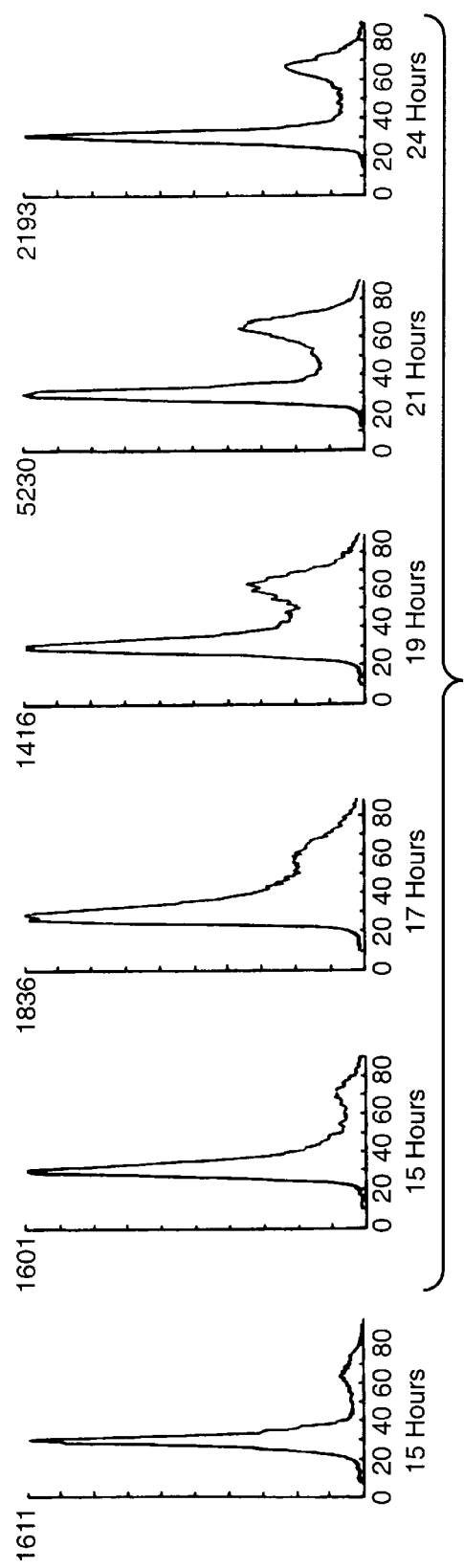
FIG._4Ea
FIG._4Eb
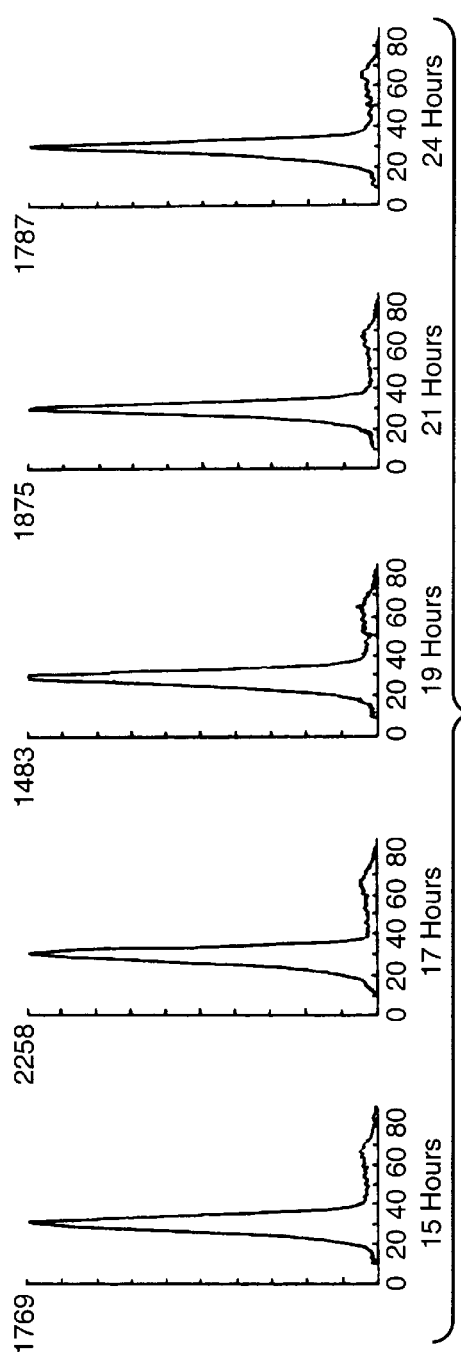
FIG._4Ec

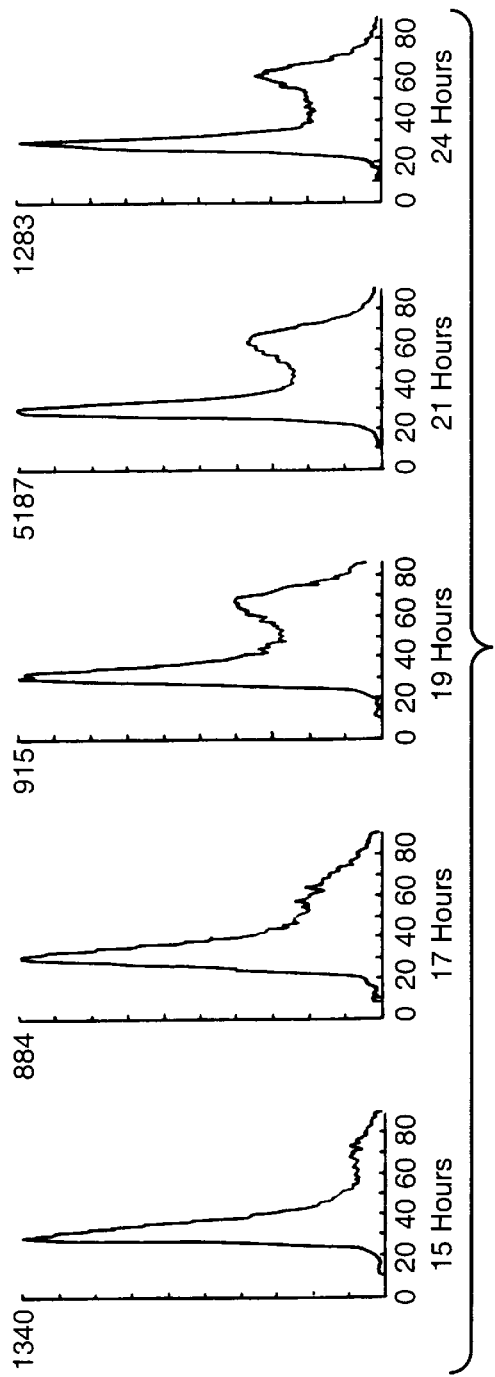
FIG._4Ed
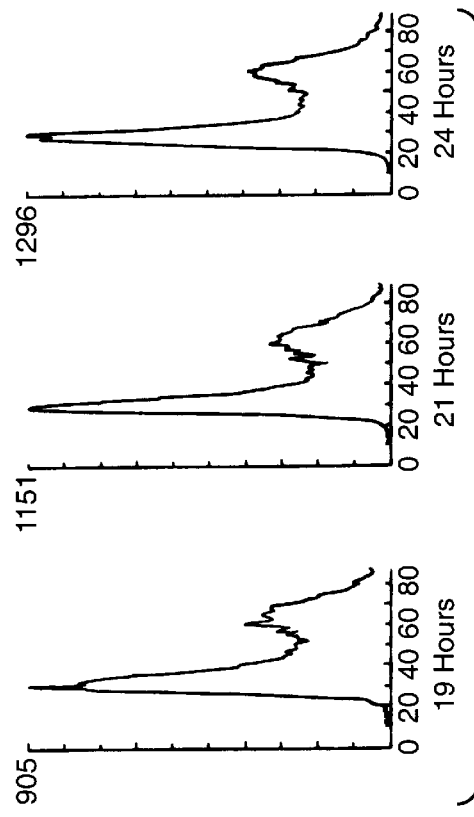
FIG._4Ee

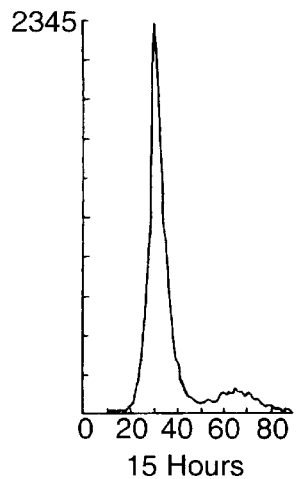
FIG._5Ba
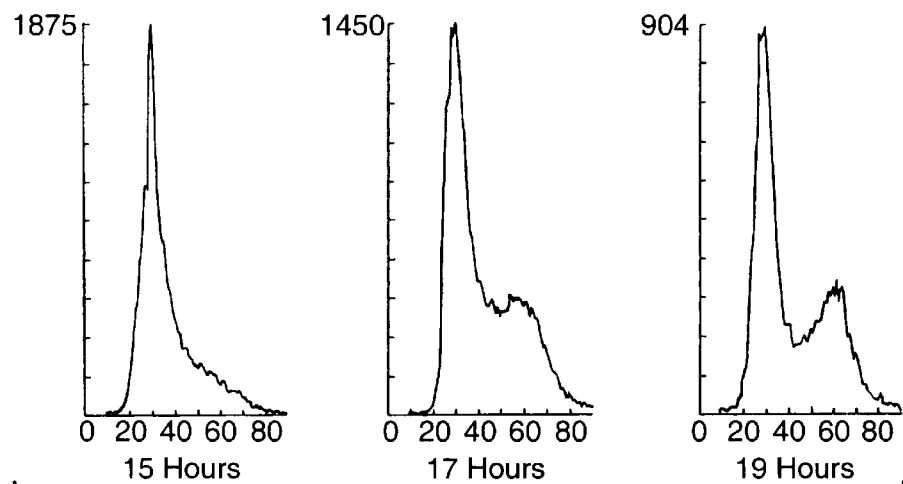
FIG._5Bb
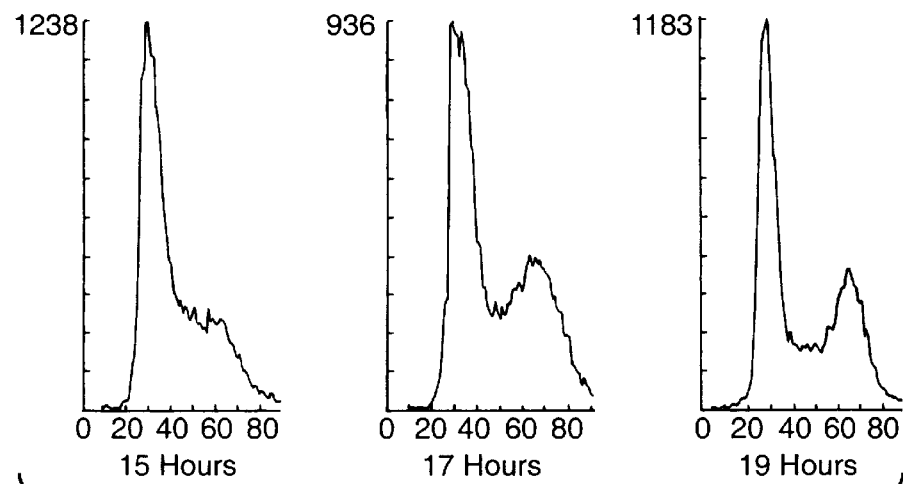
FIG._5Bc

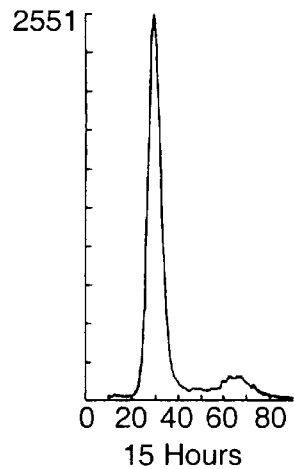
FIG._5Aa
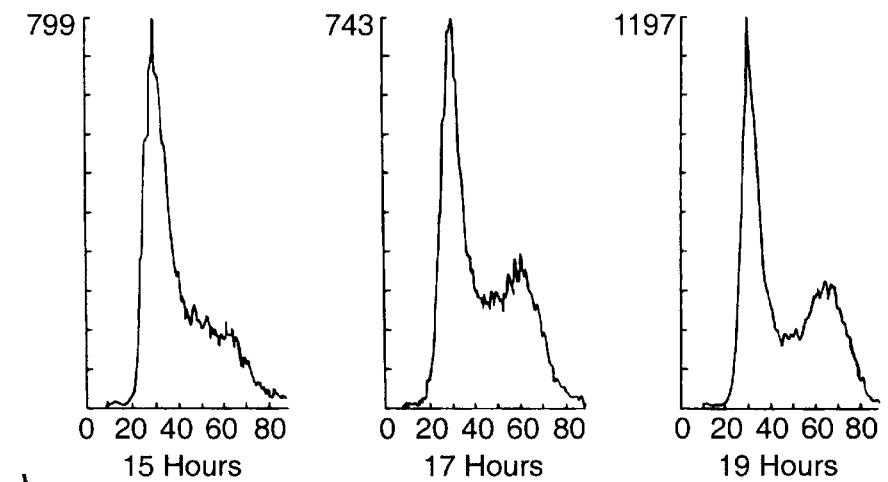
FIG._5Ab
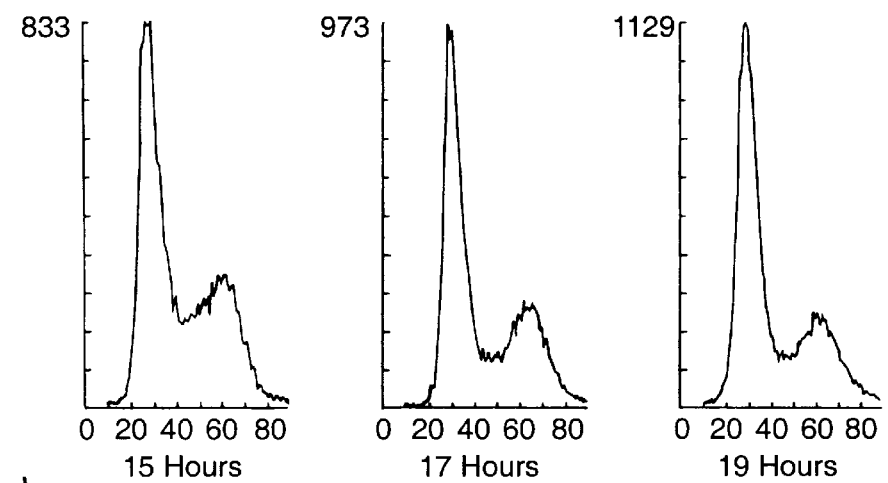
FIG._5Ac

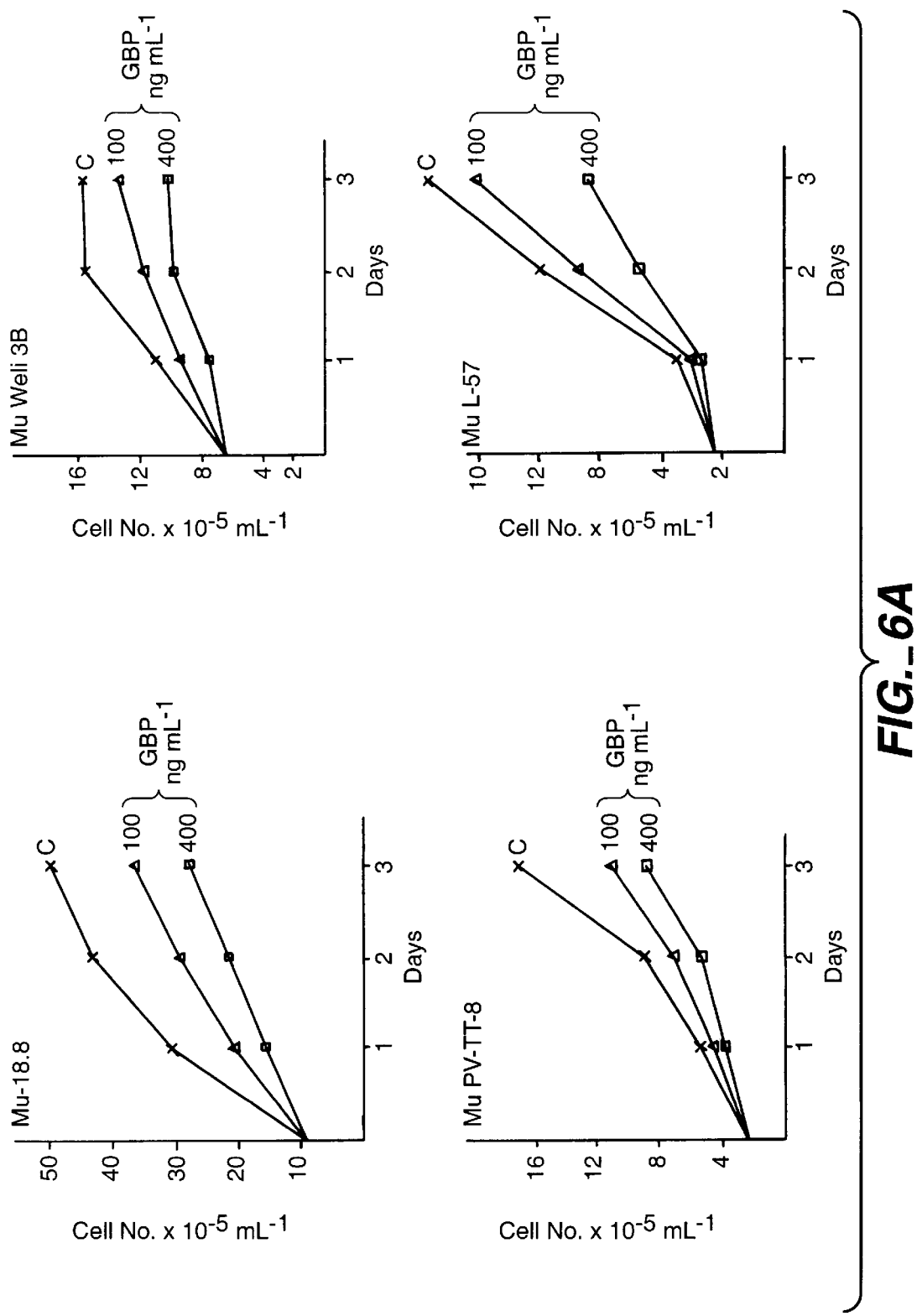
FIG._6A

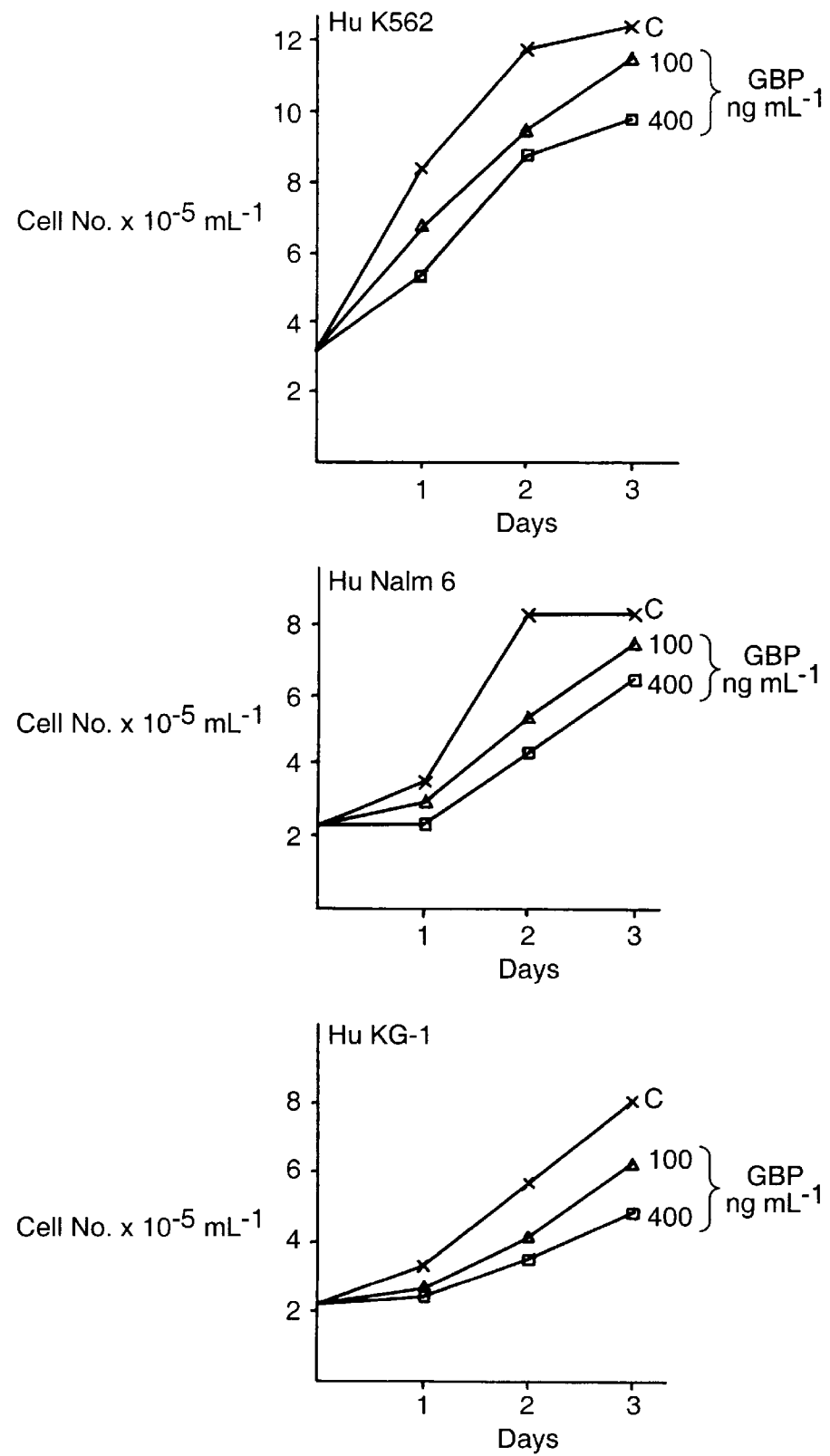
*FIG._6B*

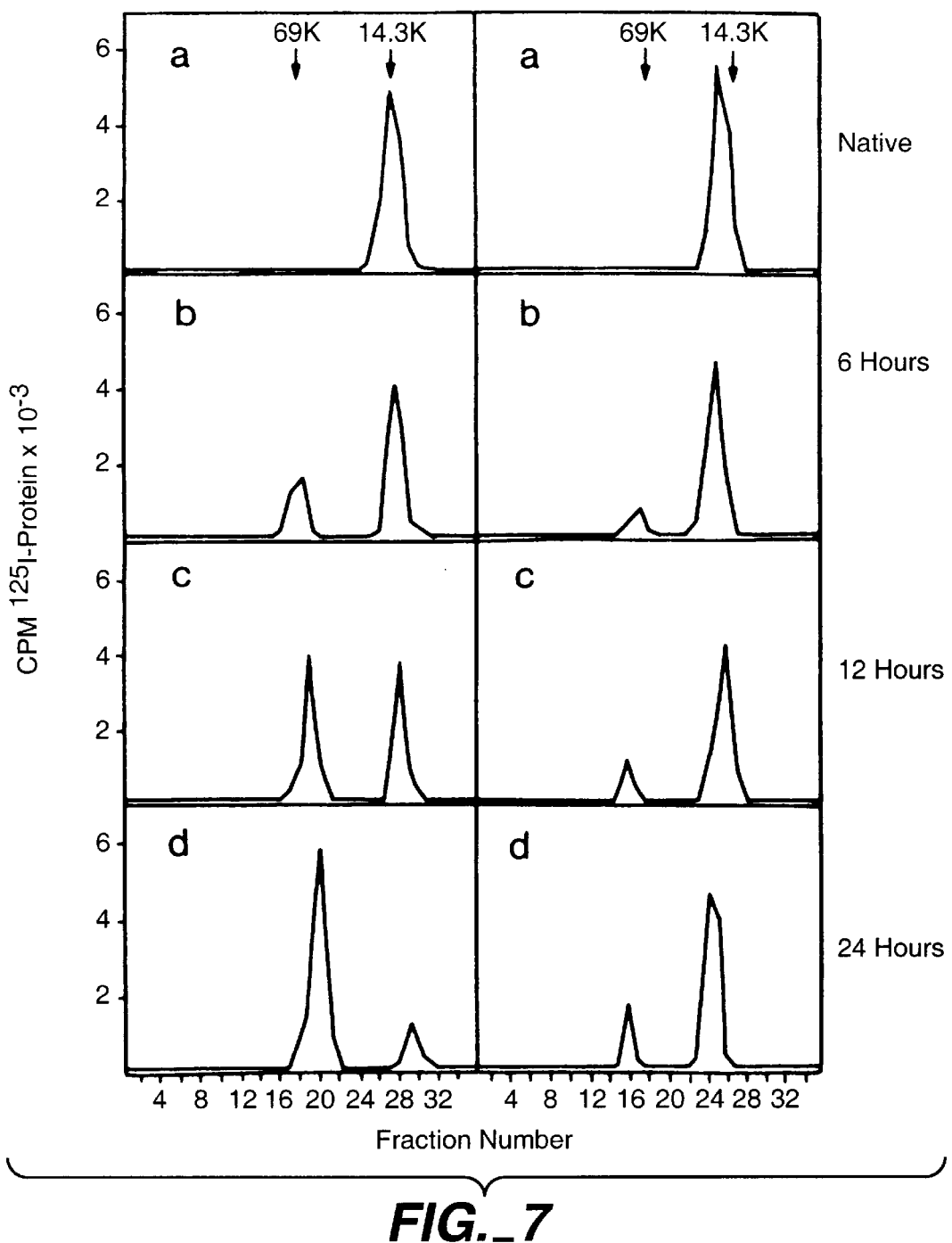
FIG._7

FIG._8A
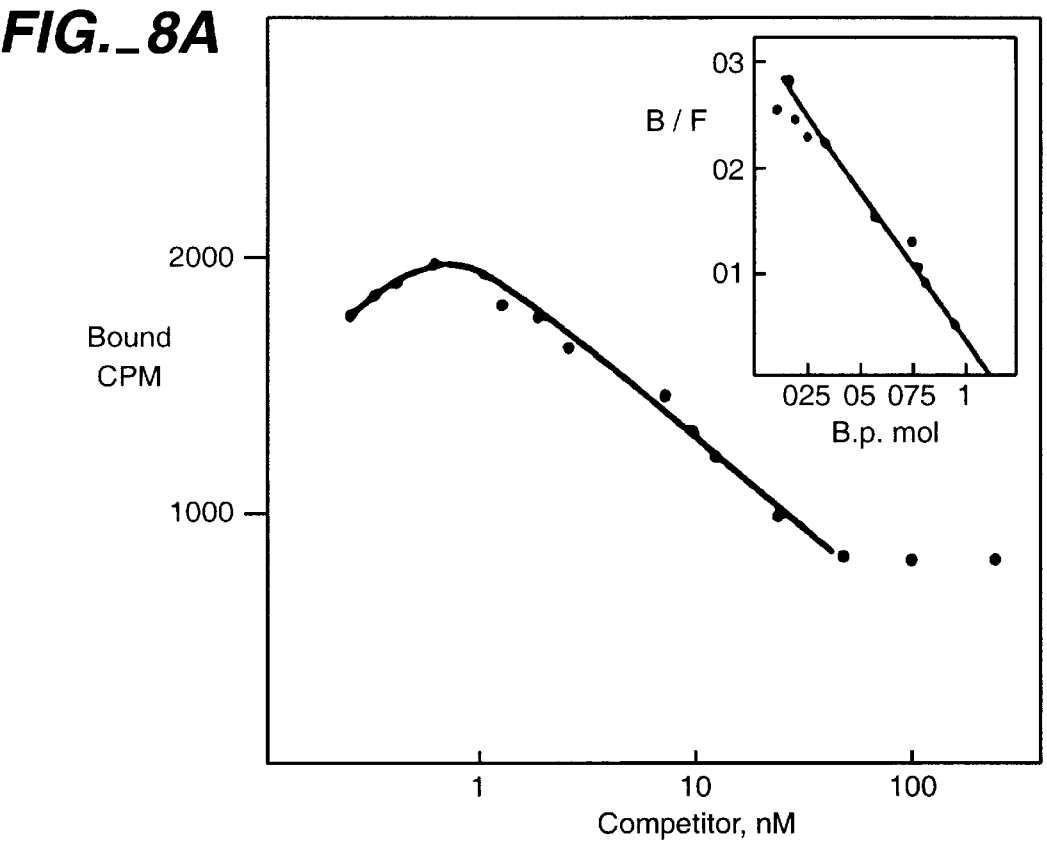
FIG._8B
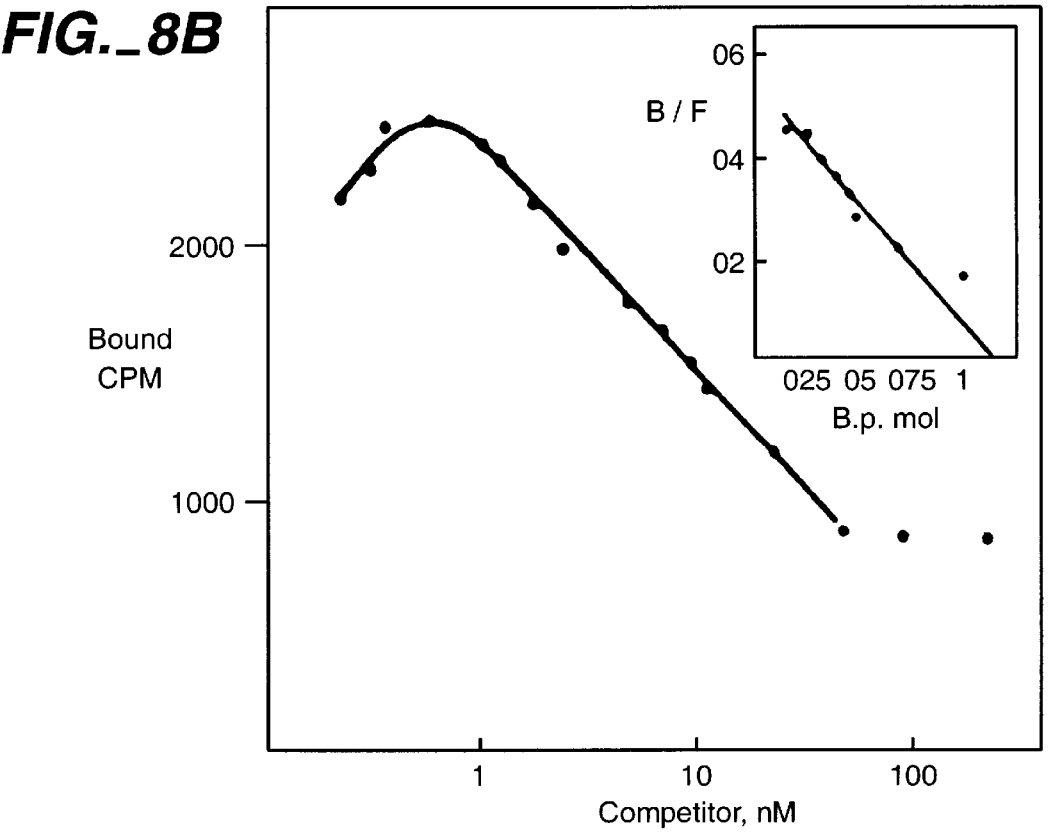

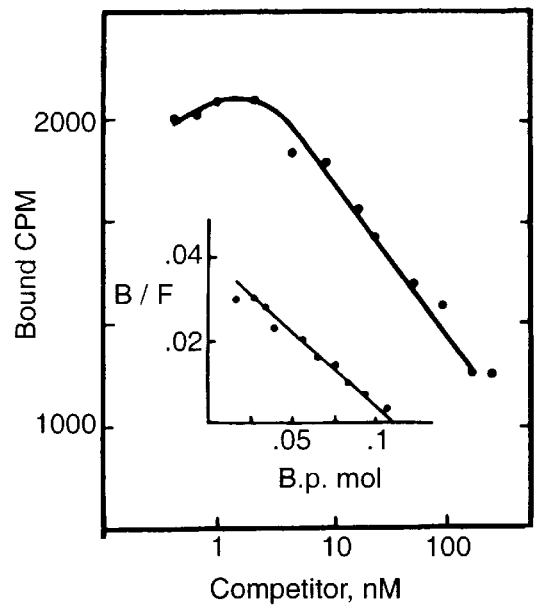
FIG._8Ca
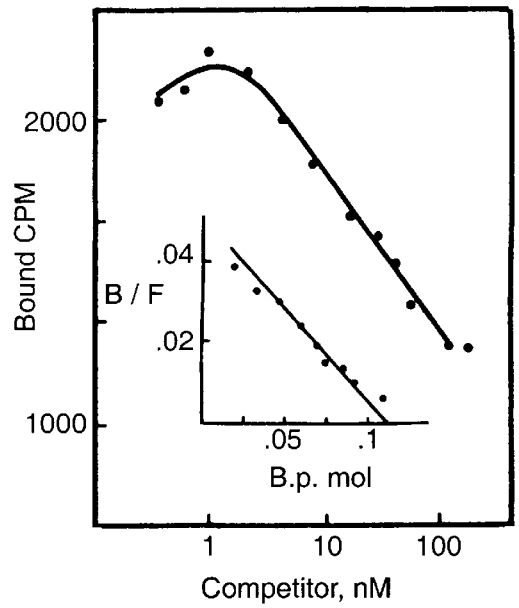
FIG._8Cb
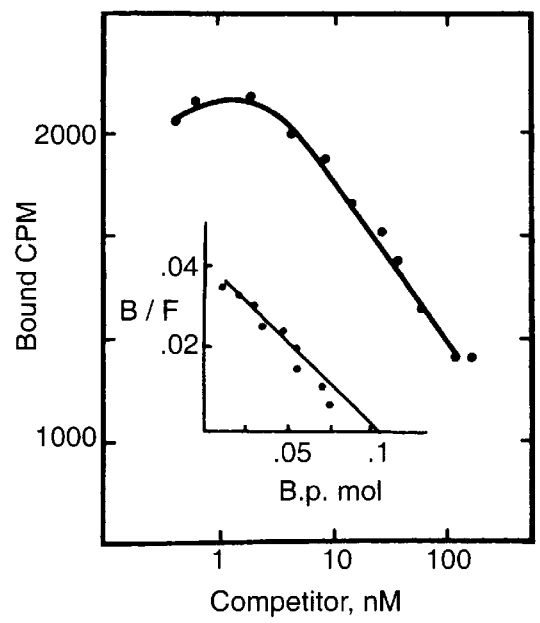
FIG._8Cc
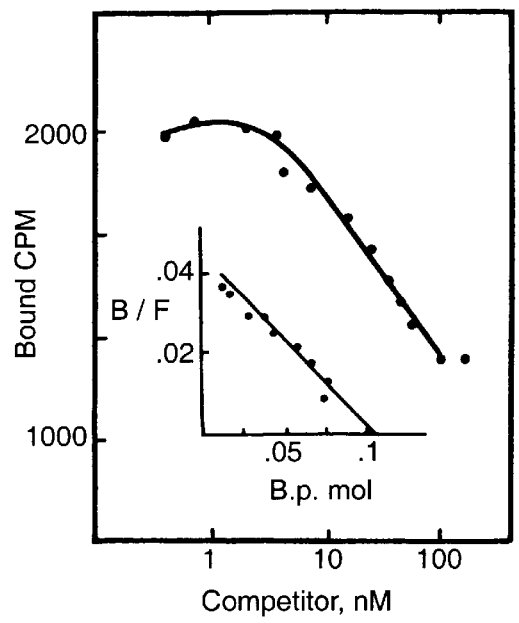
FIG._8Cd

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 7 residues
      (B) TYPE: amino acid
      (C) STRANDEDNESS:
      (D) TOPOLOGY: linear (ii) MOLECULE TYPE:
            (A) DESCRIPTION: peptide (xi) SEQUENCE DESCRIPTION: SEQ ID NO:1:

Ser Phe Val Leu Asn Leu Gly
1               5

(2) INFORMATION FOR SEQ ID NO:2:

(i) SEQUENCE CHARACTERISTICS:
            (A) LENGTH: 13 residues
            (B) TYPE: amino acid
            (C) STRANDEDNESS:
            (D) TOPOLOGY: linear (ii) MOLECULE TYPE:
            (A) DESCRIPTION: peptide (xi) SEQUENCE DESCRIPTION: SEQ ID NO:2:

Phe Asn Ala His Gly Asp Ala Asn Thr Ile Val Cys Asn
1               5                   10

(2) INFORMATION FOR SEQ ID NO:3:

(i) SEQUENCE CHARACTERISTICS:
            (A) LENGTH: 12 residues
            (B) TYPE: amino acid
            (C) STRANDEDNESS:
            (D) TOPOLOGY: linear (ii) MOLECULE TYPE:
            (A) DESCRIPTION: peptide (xi) SEQUENCE DESCRIPTION: SEQ ID NO:3:

Asn Met Glu Ala Ile Asn Tyr Met Ala Ala Asp Gly
1               5                   10

(2) INFORMATION FOR SEQ ID NO:4:

(i) SEQUENCE CHARACTERISTICS:
            (A) LENGTH: 7 residues
            (B) TYPE: amino acid
            (C) STRANDEDNESS:
            (D) TOPOLOGY: linear (ii) MOLECULE TYPE:
            (A) DESCRIPTION: peptide (xi) SEQUENCE DESCRIPTION: SEQ ID NO:4:

Gly Phe Val Ile Asn Leu Gly
1               5

(2) INFORMATION FOR SEQ ID NO:5:

(i) SEQUENCE CHARACTERISTICS:
            (A) LENGTH: 5 residues
            (B) TYPE: amino acid
            (C) STRANDEDNESS:
            (D) TOPOLOGY: linear (ii) MOLECULE TYPE:
            (A) DESCRIPTION: peptide (xi) SEQUENCE DESCRIPTION: SEQ ID NO:5:

Phe Ser Gly Ser Thr
1               5

(2) INFORMATION FOR SEQ ID NO:6:

(i) SEQUENCE CHARACTERISTICS:
             (A) LENGTH: 4 residues
             (B) TYPE: amino acid
             (C) STRANDEDNESS:
             (D) TOPOLOGY: linear (ii) MOLECULE TYPE:
             (A) DESCRIPTION: peptide (xi) SEQUENCE DESCRIPTION: SEQ ID NO:6:

Ile Val Cys Asn
 1

(2) INFORMATION FOR SEQ ID NO:7:

(i) SEQUENCE CHARACTERISTICS:
             (A) LENGTH: 12 resides
             (B) TYPE: amino acid
             (C) STRANDEDNESS:
             (D) TOPOLOGY: linear (ii) MOLECULE TYPE:
             (A) DESCRIPTION: peptide (xi) SEQUENCE DESCRIPTION: SEQ ID NO:7:

Gly His Ser Met Leu Ser Tyr Glu Ser Ile Arg Gly
 1               5                  10

(2) INFORMATION FOR SEQ ID NO:8:

(i) SEQUENCE CHARACTERISTICS:
             (A) LENGTH: 12 residues
             (B) TYPE: amino acid
             (C) STRANDEDNESS:
             (D) TOPOLOGY: linear (ii) MOLECULE TYPE:
             (A) DESCRIPTION: peptide (xi) SEQUENCE DESCRIPTION: SEQ ID NO:8:

Asn Leu Glu Ala Ile Asn Tyr Met Ala Ala Asp Gly
 1               5                  10

(2) INFORMATION FOR SEQ ID NO:9:

(i) SEQUENCE CHARACTERISTICS:
             (A) LENGTH: 7 residues
             (B) TYPE: amino acid
             (C) STRANDEDNESS:
             (D) TOPOLOGY: linear (ii) MOLECULE TYPE:
             (A) DESCRIPTION: peptide (xi) SEQUENCE DESCRIPTION: SEQ ID NO:9:

Ser Phe Leu Leu Asn Leu Gly
 1               5

(2) INFORMATION FOR SEQ ID NO:10:

(i) SEQUENCE CHARACTERISTICS:
             (A) LENGTH: 13 residues
             (B) TYPE: amino acid
             (C) STRANDEDNESS:
             (D) TOPOLOGY: linear (ii) MOLECULE TYPE:
             (A) DESCRIPTION: peptide (xi) SEQUENCE DESCRIPTION: SEQ ID NO:10:

```
Phe Asn Ala His Gly Asp Val Asn Leu Ile Val Ser Asn
1               5                   10
```

(2) INFORMATION FOR SEQ ID NO:11:

(i) SEQUENCE CHARACTERISTICS:
        (A) LENGTH: 12 residues
        (B) TYPE: amino acid
        (C) STRANDEDNESS:
        (D) TOPOLOGY: linear (ii) MOLECULE TYPE:
        (A) DESCRIPTION: peptide (xi) SEQUENCE DESCRIPTION: SEQ ID NO:11:

```
Asn Leu Glu Ala Ile Asn Tyr Leu Ser Ala Gly Gly
1               5                   10
```

(2) INFORMATION FOR SEQ ID NO:12:

(i) SEQUENCE CHARACTERISTICS:
        (A) LENGTH: 7 residues
        (B) TYPE: amino acid
        (C) STRANDEDNESS:
        (D) TOPOLOGY: linear (ii) MOLECULE TYPE:
        (A) DESCRIPTION: peptide (xi) SEQUENCE DESCRIPTION: SEQ ID NO:12:

```
Ser Phe Val Met Asn Leu Gly
1               5
```

(2) INFORMATION FOR SEQ ID NO:13:

(i) SEQUENCE CHARACTERISTICS:
        (A) LENGTH: 13 residues
        (B) TYPE: amino acid
        (C) STRANDEDNESS:
        (D) TOPOLOGY: linear (ii) MOLECULE TYPE:
        (A) DESCRIPTION: peptide (xi) SEQUENCE DESCRIPTION: SEQ ID NO:13:

```
Phe Asp Ala His Gly Asp Val Asn Leu Ile Val Cys Asn
1               5                   10
```

(2) INFORMATION FOR SEQ ID NO:14:

(i) SEQUENCE CHARACTERISTICS:
        (A) LENGTH: 11 residues
        (B) TYPE: amino acid
        (C) STRANDEDNESS:
        (D) TOPOLOGY: linear (ii) MOLECULE TYPE:
        (A) DESCRIPTION: peptide (xi) SEQUENCE DESCRIPTION: SEQ ID NO:14:

```
Gly Leu Ser Phe Asp Tyr Phe Asp Thr His Gly
1               5                   10
```

(2) INFORMATION FOR SEQ ID NO:15:

(i) SEQUENCE CHARACTERISTICS:
        (A) LENGTH: 7 residues
        (B) TYPE: amino acid
        (C) STRANDEDNESS:
        (D) TOPOLOGY: linear (ii) MOLECULE TYPE:
         (A) DESCRIPTION: peptide (xi) SEQUENCE DESCRIPTION: SEQ ID NO:15:

Asn Leu Glu Ala Ile Asn Tyr
1               5

(2) INFORMATION FOR SEQ ID NO:16:

(i) SEQUENCE CHARACTERISTICS:
         (A) LENGTH: 135 residues
         (B) TYPE: amino acid
         (C) STRANDEDNESS:
         (D) TOPOLOGY: linear (ii) MOLECULE TYPE:
         (A) DESCRIPTION: peptide (xi) SEQUENCE DESCRIPTION: SEQ ID NO:16:

Ala Cys Gly Leu Val Ala Ser Asn Leu Asn Leu Lys Pro Gly Glu
1               5                  10                  15

Cys Leu Lys Val Arg Gly Glu Val Ala Ser Asp Ala Lys Ser Phe
                20                  25                  30

Val Leu Asn Leu Gly Lys Asp Ser Asn Asn Leu Cys Leu Glu Glu
                35                  40                  45

Met Pro Arg Glu Asn Ala His Gly Asp Ala Asn Thr Ile Val Cys
                50                  55                  60

Ile Thr Lys Glu Asp Gly Thr Trp Gly Thr Glu His Pro Glu Pro
                65                  70                  75

Ala Phe Pro Glu Gln Pro Gly Ser Ile Thr Glu Val Cys Ile Thr
                80                  85                  90

Phe Asp Gln Ala Asp Leu Thr Ile Lys Leu Pro Asp Gly His Glu
                95                  100                 105

Glu Phe Lys Phe Pro Asn Arg Leu Asn Met Glu Ala Ile Asn Tyr
                110                 115                 120

Met Ala Ala Asp Gly Asp Phe Lys Ile Lys Cys Val Ala Phe Glu
                125                 130                 135

(2) INFORMATION FOR SEQ ID NO:17:

(i) SEQUENCE CHARACTERISTICS:
         (A) LENGTH: 497 bases
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:17:

CTTCGCTTCA GCTTCAATC ATG GCC TGT GGT CTG GTC GCC AGC AAC CTG            49
                    Met Ala Cys Gly Leu Val Ala Ser Asn Leu
                    1               5                   10

AAT CTC AAA CCT GGG GAA TGT CTC AAA GTT CGG GGA GAG GTG GCC TCG         97
Asn Leu Lys Pro Gly Glu Cys Leu Lys Val Arg Gly Glu Val Ala Ser
                15                  20                  25

GAC GCC AAG AGC TTT GTG CTG AAC CTG GGA AAA GAC AGC AAC AAC CTG         145
Asp Ala Lys Ser Phe Val Leu Asn Leu Gly Lys Asp Ser Asn Asn Leu
                30                  35                  40

TGC CTA CAC TTC AAT CCT CGC TTC AAT GCC CAT GGA GAC GCC AAC ACC         193
Cys Leu His Phe Asn Pro Arg Phe Asn Ala His Gly Asp Ala Asn Thr
                45                  50                  55

```
ATT GTG TGT AAC ACC AAG GAA CAT GGG ACC TGG GGA ACC GAA CAC CGG         241
Ile Val Cys Asn Thr Lys Glu Asp Gly Thr Trp Gly Thr Glu His Arg
        60                  65                  70

GAA CCT GCC TCC CCT TTC CAG CCT GGG AGC ATC ACA GAG GTG TGC ATC         289
Glu Pro Ala Phe Pro Phe Gln Pro Gly Ser Ile Thr Glu Val Cys Ile
 75                  80                  85                  90

AAC TTT GAC CAG GCT GAC CTG ACC ATC AAG CTG CCA GAC GGA CAT GAA         337
Thr Phe Asp Gln Ala Asp Leu Thr Ile Lys Leu Pro Asp Gly His Glu
                 95                 100                 105

TTC AAG TTC CCA AAC CGC CTC AAC ATG GAG GCC ATC AAC TAC ATG GCG         385
Phe Lys Phe Pro Asn Arg Leu Asn Met Glu Ala Ile Asn Tyr Met Ala
            110                 115                 120

GCG GAT GGA GAC TTC AAG ATT AAG TGC GTG GCC TTT GAG TGAAGCCAGC          434
Ala Asp Gly Asp Phe Lys Ile Lys Cys Val Ala Phe Glu
        125                 130                 135

CAGCCTGTAG CCCTCAATAA AAGGCAGCTG CCTCTGCTCC CCATAAAAAA AAAAAAA         491

AAAAAA                                                                  497

(2) INFORMATION FOR SEQ ID NO:18:

(i) SEQUENCE CHARACTERISTICS:
        (A) LENGTH: 135 residues
        (B) TYPE: amino acid
        (C) STRANDEDNESS:
        (D) TOPOLOGY: linear (ii) MOLECULE TYPE:  peptide (xi) SEQUENCE DESCRIPTION:  SEQ ID NO:18:

Met Ala Cys Gly Leu Val Ala Ser Asn Leu Asn Leu Lys Pro Gly
 1               5                  10                  15

Glu Cys Leu Lys Val Arg Gly Glu Val Ala Ser Asp Ala Lys Ser
                20                  25                  30

Phe Val Leu Asn Leu Gly Lys Asp Ser Asn Asn Leu Cys Leu His
                35                  40                  45

Phe Asn Pro Arg Phe Asn Ala His Gly Asp Ala Asn Thr Ile Val
                50                  55                  60

Cys Asn Thr Lys Glu Asp Gly Thr Trp Gly Thr Glu His Arg Glu
                65                  70                  75

Pro Ala Phe Pro Phe Gln Pro Gly Ser Ile Thr Glu Val Cys Ile
                80                  85                  90

Thr Phe Asp Gln Ala Asp Leu Thr Ile Lys Leu Pro Asp Gly His
                95                 100                 105

Glu Phe Lys Phe Pro Asn Arg Leu Asn Met Glu Ala Ile Asn Tyr
               110                 115                 120

Met Ala Ala Asp Gly Asp Phe Lys Ile Lys Cys Val Ala Phe Glu
               125                 130                 135

(2) INFORMATION FOR SEQ ID NO:19:

(i) SEQUENCE CHARACTERISTICS:
        (A) LENGTH: 476 bases
        (B) TYPE: nucleic acid
        (C) STRANDEDNESS: double
        (D) TOPOLOGY: linear (ii) MOLECULE TYPE:  cDNA (xi) SEQUENCE DESCRIPTION: SEQ ID NO:19:

TGAGACAGCA GATATCAATA CACTAACATC CTCCTGGACT CAATC                       45
```

```
ATG GCT TGT GGT CTG GTC GCC AGC AAC CTG AAT CTC AAA CCT GGA GAG        93
Met Ala Cys Gly Leu Val Ala Ser Asn Leu Asn Leu Lys Pro Gly Glu
 1               5                  10                  15

TGC CTT CGA GTG CGA GGC GAG GTG GCT CCT GAC GCT AAG AGC TTC GTG       141
Cys Leu Arg Val Arg Gly Glu Val Ala Pro Asp Ala Lys Ser Phe Val
                20                  25                  30

CTG AAC CTG GGC AAA GAC AGC AAC AAC CTG TGC CTG CAC TTC AAC CCT       189
Leu Asn Leu Gly Lys Asp Ser Asn Asn Leu Cys Leu His Phe Asn Pro
            35                  40                  45

CGC TTC AAC GCC CAC GGC GAC GCC AAC ACC ATC GTG TGC AAC AGC AAG       237
Arg Phe Asn Ala His Gly Asp Ala Asn Thr Ile Val Cys Asn Ser Lys
        50                  55                  60

GAC GGC GGG GCC TGG GGG ACC GAG CAG CGG GAG GCT GTC TTT CCC TTC       285
Asp Gly Gly Ala Trp Gly Thr Glu Gln Arg Glu Ala Val Phe Pro Phe
 65                 70                  75                  80

CAG CCT GGA AGT GTT GCA GAG GTG TGC ATC ACC TTC GAC CAG GCC AAC       333
Gln Pro Gly Ser Val Ala Glu Val Cys Ile Thr Phe Asp Gln Ala Asn
                85                  90                  95

CTG AAC GTC AAC CTG CCA GAT GGA TAC GAA TTC AAG TTC CCC AAC CGC       381
Leu Thr Val Lys Leu Pro Asp Gly Tyr Glu Phe Lys Phe Pro Asn Arg
            100                 105                 110

CTC AAC CTG GAG GCC ATC AAC TAC ATG GCA GCT GAC GGT GAC TTC AAG       429
Leu Asn Leu Glu Ala Ile Asn Tyr Met Ala Ala Asp Gly Asp Phe Lys
        115                 120                 125

ATC AAA TGT GTG GCC TTT GAC TGAAATCAGC CACGCCATGG CCCCCG              476
Ile Lys Cys Val Ala Phe Asp
130                 135

(2) INFORMATION FOR SEQ ID NO:20:

(i) SEQUENCE CHARACTERISTICS:
        (A) LENGTH: 135 residues
        (B) TYPE: amino acid
        (C) STRANDEDNESS:
        (D) TOPOLOGY: linear (ii) MOLECULE TYPE:  peptide (xi) SEQUENCE DESCRIPTION: SEQ ID NO:20:

Met Ala Cys Gly Leu Val Ala Ser Asn Leu Asn Leu Lys Pro Gly
 1               5                  10                  15

Glu Cys Leu Arg Val Arg Gly Glu Val Ala Pro Asp Ala Lys Ser
                20                  25                  30

Phe Val Leu Asn Leu Gly Lys Asp Ser Asn Asn Leu Cys Leu His
                35                  40                  45

Phe Asn Pro Arg Phe Asn Ala His Gly Asp Ala Asn Thr Ile Val
            50                  55                  60

Cys Asn Ser Lys Asp Gly Gly Ala Trp Gly Thr Glu Gln Arg Glu
                65                  70                  75

Ala Val Phe Pro Phe Gln Pro Gly Ser Val Ala Glu Val Cys Ile
                80                  85                  90

Thr Phe Asp Gln Ala Asn Leu Thr Val Lys Leu Pro Asp Gly Tyr
                95                  100                 105

Glu Phe Lys Phe Pro Asn Arg Leu Asn Leu Glu Ala Ile Asn Tyr
                110                 115                 120

Met Ala Ala Asp Gly Asp Phe Lys Ile Lys Cys Val Ala Phe Asp
                125                 130                 135
```

NON-AGGLUTINATING β-GALACTOSIDE BINDING PROTEIN AND ITS ENCODING NUCLEIC ACID

The invention relates to proteins known as β-galactoside binding proteins and to their use to arrest, control or otherwise affect cell growth.

Proteins capable of binding specific sugars on cell surfaces have been known for many years. The sugar binding proteins hitherto known are more commonly referred to by the generic term "lectin". A lectin is defined as a carbohydrate binding protein which has a specificity for particular sugar residues, is bivalent or polyvalent with respect to sugar binding and is at least bivalent if monomeric (Barondes, H, Science 223, 1259–1264 (1984)). Due to the multivalency it is a further characterising property of lectins that they cause agglutination of red blood cells i.e. they are haemagglutinins and can also cause agglutination of other cells because of their affinity for sugars on the cell surface. Also, because of their cross-linking property, which relates to bivalency or polyvalency they can impede cell proliferation. However their effect is indiscriminate, physiologically irreversible and they are highly toxic.

Particularly well-known examples of lectins are the plant proteins Concanavalin A and phytohaemagglutinin. More recently, sugar binding proteins have been identified in many other organisms, including vertebrates and slime moulds. Vertebrate proteins in this class have been described and characterised, for example, in the following references:

Barondes, H., Science 223, 1259–1264 (1984)
Ohyama, Y., Hirabayashi, J., Oda, Y., Ohno, S., Kawasaki, H., Suzuki, K., and Kasai, K. Biochem. Biophys. Res. Comm. 134, 51–56 (1986)
Southan, C., Aitken, A., Childs, R. A., Abbott, W. M. and Feizi, T. FEBS Lett. 214, 301–304 (1987)
Hirabayashi, J and Kasai, K. J. Biochem. (Tokyo) 104, 1–4 (1988)
Clerch, L. B., Whitney, P., Hass, M., Brew, K., Miller T., Werner, R and Massaro, D. Biochemistry 27, 692–699 (1988)
Couraund, P. O., Casentini-Borocz, D., Bringman, T. S., Griffith, J., McGrogan, M. and Nedwin, G. E. J. Biol. Chem. 264, 1310–1316 (1989)
Abbott, M. W., and Feizi, T. Biochem J. 259, 291–294 (1989)

It will be apparant from the above definition of a lectin that, as β-galactosides are sugars, β-galactoside binding proteins fulfil one of the criteria of the lectins and it was hitherto understood that all β-galactoside binding proteins were in fact lectins. It is demonstrated herein by the present inventors that this is in fact not the case.

Plant lectins have been known to cause lymphocyte activation. EP-A-0337299 describes also the use of lectins from a variety of vertebrate sources in the treatment of diseases involving defects in the immune system such as myasthenia gravis and reumatoid arthritis. A beneficial effect on diabetes and multiple sclerosis is also suggested.

In EP-A-0260497 a "lectin-like" protein isolated from a cell line of *Sarcophaga peregrina* (flesh fly) is described which acts as a haemagglutinin and which has an inhibitory effect on the growth of tumours in mice.

The above documents' claims are however based on the lectin characteristics of the proteins used. The present inventors, in the search for new and improved cytostatic agents, have now isolated, purified and characterised a new cytostatic protein capable of inhibiting or arresting the growth of both normal and cancer cells, which is produced by mouse embryo fibroblasts and which does not fulfil the criteria for a lectin nature. By determination of its amino acid sequence and comparison of the sequence of isolated peptides with the known sequences of other proteins using literature and database searches it has been established that the inhibitor is a β-galactoside binding protein (GBP). This has been confirmed by cDNA cloning and expression of the protein in recombinant form.

It has further been discovered by the inventors that the protein is not a lectin in accordance within the classical definition because it is monomeric and because it is monovalent with respect to sugar binding sites or it has no available sugar binding site because it is masked by a glycan complex. It is thus incapable of causing blood cells or other cells to agglutinate. Furthermore it does not exist in dimeric form as reported for the lectins but rather as a native monovalent monomer. Alternatively, it can form tetramers in which the four β-galactoside binding sites are internal and thus not available to cause cell agglutination, even where no glycan complex is associated with the molecule. Furthermore the cytostatic effect is not exerted through the sugar binding site but is exerted through domains which bind with high specific affinity to specific cell surface receptors.

The invention described herein is based on the aforementioned discoveries and also on the further discovery that the cytostatic and non-agglutinating GBP from mouse embryo fibroblasts has an inhibitory effect on growth of human cancer cells. The invention is thus directed to embodiments of these discoveries, i.e. non-agglutinating GBP's having the properties hereinbefore described, whether from natural animal sources or produced by recombinant DNA technology, for use as inhibitors and regulators of cell growth and as therapeutic agents. Although this new cell growth inhibitory protein has been isolated from mouse tissue it is to be expected that equivalent proteins having the same properties can be isolated from other species.

Thus in accordance with the invention a non-agglutinating β-galactoside-binding protein (GBP) of animal origin is provided which is free from cell-derived contamination and/or is produced by recombinant DNA technology. The protein is suitable for use as an inhibitor of growth of vertebrate cells.

It is to be understood that herein the term β-galactoside binding protein means a material having the amino acid sequence of the native protein or any modification thereof which maintains the domain or domains with capacity to bind the specific cell surface receptors of the target cell. Such modifications may include proteins which have amino acids added or removed or having changes to amino acids which do not effect the growth inhibitory activity thereof.

Further as used herein the term non-agglutinating describes a protein which in native form has an affinity for binding sugar but which is incapable of causing cell agglutination as the direct result of that sugar binding affinity. Thus GBP's capable of causing agglutination by some other biochemical mechanism are not excluded.

Preferably the GBP for use in the invention is from a vertebrate source but GBP's from other sources are not excluded.

Preferably the cells are transformed cells and more preferably transformed cells of human origin. It is to be understood that the term 'transformed cells' includes within its definition, cancer cells, all forms of malignant cells and all cells from benign tumours as well as pre-malignant, pre-transformed, hyperplastic and all irregular and undesired forms of cell proliferation. In particular the recombinant GBP's of human or animal origin may be used as therapeutic agents in the treatment of human malignant diseases. Preferably the GBP for such use will have or include an amino acid sequence of a GBP of either human or mouse origin although sequences originating from other species are not excluded. Both the native mouse and human GBP consist of 134 amino acids and share 89% homology. It has been clearly demonstrated by the present applicants that there is a cross species effect: i.e. mouse GBP inhibits growth of human cancer cells. Thus a GBP of either human or mouse origin, as well as other species, may be used as a therapeutic agent in humans or other animal species. It is to be expected that GBP's from other species will also have an inhibitory effect on the growth of human cells because a high degree of amino acid sequence homology has been demonstrated between the human non-agglutinating β-galactoside binding protein and GBP's from other species. Accordingly, such other GBP's are within the scope of the invention.

It is further demonstrated herein with reference to the recombinant mouse GBP that these proteins have the effect of maintaining cells in G0 and of preventing or reducing traverse through the G2 phase of the cell cycle and hence entry into mitosis. This particular property of the protein can be particularly advantageous from the point of view of therapy against malignant cells in G0 which are prevented from resuming growth and against proliferating malignant cells.

Furthermore the non-agglutinating property of these GBP's makes them suitable as therapeutic agents because agglutination of cells in body fluids and in tissues when a protein is given therapeutically is of course undesirable.

The GBP's for use in the invention may be monomeric and monovalent with regard to β-galactoside binding sites but preferably are monomeric with the single sugar valency masked, modified or removed altogether. They may also be polymeric and preferably tetrameric but with no sugar valency exposed. It will be understood from the information given herein that the tetrameric form is still non-agglutinating (as herein defined) and therefore within the scope of the invention. Both the monomeric and tetrameric forms may be associated with a saccharide or a saccharide complex, preferably a polysaccharide complex such as a glycan complex, but non-saccharide complexes are not excluded.

Most preferred saccharide complexes are those containing sialic acid which protects the complex associated GBP from clearance from the circulation by carbohydrate specific receptors on macrophages, hepatocytes or by other clearance systems.

A saccharide complex can be acquired, as in the case presented herein by way of example, or it can orginate within the molecule from a glycosylation site whether natural or engineered. It is envisaged that by the technique of site directed mutagenesis a glycosylation site can be created in order to allow masking of the saccharide binding site or that a complex other than a saccharide complex can be used or engineered in order to mask the saccharide binding site. Such a protein where the saccharide binding site is occluded has a therapeutic advantage for the reasons already mentioned and because of its stability and greater growth inhibitory activity. A GBP in which the β-galactoside binding site is masked by a complex is hereinafter described as the "complexed" form of the protein. This term is used whether the complex is acquired, as in the case described herein, or whether it originates within the molecule from for example a glycosylation site.

It is of course further envisaged that the β-galactoside binding protein, in accordance with the invention may be modified such that the saccharide binding site, rather than being masked is removed altogether. Such proteins are still within the scope of the invention.

In accordance with another aspect of the invention there is provided a pharmaceutical composition which comprises an effective amount of a non-agglutinating β-galactoside binding protein of animal origin together with a carrier or diluent. Preferably the composition is formulated for parenteral administration or for other routes and may include any diluent, adjuvent, preservative or other component conventionally included in such compositions and well-known to those skilled in the art. Where the composition is formulated in unit dosage form it is preferably such that the patient receives from 10 ng to 1000 mg per dose, depending on the particular therapeutic use and the sensitivity of the target cells.

The GBP may also be used tagged or attached to another protein or molecular carrier.

In accordance with a third aspect of the invention there is provided a method of producing a non-agglutinating β-galactoside binding protein as defined herein which method comprises at least the steps of:

(a) providing an organism, either unicellular or multicellular which expresses said protein, (b) allowing expression of said protein, (c) separating and identifying said protein in impure form from said organism, and (d) subjecting said protein to a purification procedure to produce a product substantially free from contamination derived from the expressing organism.

The organism which produces the GBP may comprise animal cells which express the protein constitutively and can be cultivated to produce the protein on a commercial scale. A wide range of animal cell lines may be used to produce GBP in this manner including those originating from insects, fish, humans and other mammals. The constitutively expressed protein can be readily harvested, identified and purified from tissue culture medium in which the cells lines are grown by standard techniques known to the man skilled in the art. Particularly preferred for commercial production of GBP are continous cell lines, especially those which grow in suspension culture.

In the examples described herein the inventors have for convenience harvested and purified GBP from secondary mouse embryo fibroblasts.

Alternatively the organism which produces the GBP may be one which has been engineered by recombinant DNA technology to produce the protein. Such organisms will include all the constitutively producing cell lines referred to above which have been engineered to give an improved yield and also a wide range of organisms, both unicellular and multicellular which would not normally express the protein but which have had the DNA coding for GBP introduced therein. Particularly preferred in this regard are microorganisms such as bacteria, yeasts and fungi or-plant and animal tissue culture cells but use of higher organisms such as plants and animals is also envisaged. The genetic engineering procedures required to introduce a foreign gene into a microorganism and obtain expression thereof are well-known to the skilled man in the art.

In the examples described herein the inventors have used a CDM8 plasmid as an expression vector, and the murine recombinant protein is expressed in COS-1 cells.

It is also envisaged that GBP's may be isolated directly from animal tissues. Thus in accordance with a fourth aspect of the invention there is provided a method of producing a non-agglutinating GBP as defined herein comprising at least the steps of:

(a) treating tissue of animal origin to obtain a protein extract therefrom,
(b) separating and identifying the non-agglutinating β-galactoside binding protein from said extract, and
(c) subjecting said protein to a purification procedure to produce a product substantially free from tissue derived contamination.

The protein may be extracted, separated and purified by any one of a number of well-known techniques. In particular it is possible and indeed preferable to make use of the GBP's sugar binding capacity to effect separation of the protein from other proteins released from the tissue. It is preferable if the tissues in question are human tissues and in this regard human placental tissue is particularly suitable because it is readily available. Further, placental tissue from other large mammals such as for example, cows, pigs etc. may be used as a source of GBP as they are also available in plentiful supply.

Alternatively GBP or any part thereof may be prepared synthetically.

In connection with the production of a recombinant GBP the following have been deposited at the National Collection of Type Cultures, 61 Colindale Avenue, London NW9 5AT on Apr. 26, 1989:

a) *E. Coli* MC 1061/p3 hosting CDM8 plasmid containing full cDNA coding sequence of murine GBP.
   Accession No. 12237
b) bacteriophage λgt 11 containing full cDNA coding sequence of human GBP. Accession No. 12236.
c) *E. coli* Y 1090 as host for b). Accession No. 12235

The availability of the above provides means for the skilled man as a matter of routine, to make constructs for the expression of animal GBP's from other sources by simple substitution of the cDNA inserts or to express mouse or human GBP's using other vectors. The above plasmid and phage provide models for the construction of other vectors and the expression of other GBP's which can be optionally engineered to have the sugar binding site masked, altered or removed.

Although the GBP's of the invention may be produced by a wide variety of methods as discussed above, the preparation and isolation of natural and of recombinant mouse GBP for use in accordance with the invention was carried out by the inventors by first culturing secondary mouse embryo fibroblasts (MEF) and harvesting the culture medium. The natural protein was purified therefrom by Sephadex gel filtration followed by reverse phase HPLC. Synchronous cultures of mouse embryo fibroblasts were used as test cells to detect cell growth inhibitory activity and the degree of inhibition was assessed by direct counting of cells and by cell cycle analysis employing cytofluorometry.

The protein was characterised by first obtaining the amino acid sequence of three peptides by standard procedures and then searching in the literature and through a protein database for proteins containing regions of homology with the sequenced peptides. It was thus established that the newly isolated protein was β-galactoside binding protein. This was confirmed by cDNA cloning and use of the recombinant protein for further characterization studies.

A phage λgt 10 cDNA library was constructed using mouse embryo fibroblast mRNA as the nucleic acid source. The knowledge of the peptide amino acid sequences allowed oligonucleotide probes to be synthesised to screen the library. From this exercise a cDNA of 110 bp was obtained which served as a further probe for a CDM8 plasmid library constructed from size fractionated cDNAs. By this route a clone was identified having a cDNA insert encoding the amino-terminal methionine and a protein of 134 amino acids with a translated molecular weight of 14,735 Daltons. The CDM8 plasmid carrying mouse GBP cDNA was used to transfect COS-1 cells in which expression of recombinant mouse GBP (rGBP) was achieved. The recombinant protein was purified using anti-mouse GBP antibodies raised by the inventors although any one of a number of standard purification methods could have been used. Mouse GBP was shown to have potent growth inhibitory activity on normal mouse cells, mouse transformed and cancer cells and human cancer cells. Further, mouse GBP has been shown to have an inhibitory effect on viral replication and is anticipated to have a regulatory effect on cells of the immune system.

The detailed procedures set out hereinafter are by way of example of the route to the animal GBP's, both natural and recombinant, for use in accordance with the invention.

BRIEF DESCRIPTION OF THE DRAWINGS

Reference is made to the accompanying drawings in which:

FIG. 1A shows a reverse phase HPLC tracing in which two peaks of cell growth inhibitory activity were identified corresponding to the complexed (Mr 18,000) and non-complexed (Mr 15,000) forms for the protein, FIG. 1B shows protein bands from the fractions corresponding to the peaks as shown by SDS gradient polyacrylamide gel electrophoresis(PAGE) and Biorad silver staining, FIG. 1C shows the re-isolation of the protein on a 12% SDS gel from fractions eluted from the preceding polyacrylamide gel as shown in FIG. 1B, FIG. 1D*a* shows protein bands obtained on SDS gradient polyacrylamide gel electrophoresis under reducing and non-reducing conditions of recombinant protein expressed in COS-1 cells.

FIG. 1D*b* shows a protein blot stained with a glycan stain comparing staining of the 18,000 and 15,000 Mr GBP's of the invention with the glycosylated protein transferrin and the non-glycosylated N terminus fragment of transferrin.

FIG. 1E shows protein bands obtained on an SDS gradient polyacrylamide gel elecrophoresis after treatment of 18,000 Mr GBP with a competing sugar, with neuraminidase and with an enzyme which breaks O saccharide/protein bonds.

FIG. 2A shows the amino acid sequence of three peptides (SEQ ID NOS: 1–3) and the homology of these peptides with amino acid sequences of β-galactoside binding protein from vertebrate sources (SEQ ID NOS: 4–15), lack of homology being limited to the boxed symbols, FIG. 2B*a* shows the amino acid sequence of mouse GBP (SEQ ID NO: 16) with the sugar binding site underlined and the deduced secondary structure, FIG. 2B*b* is a hydropathic profile of the protein with the saccharide binding region in closed symbols, FIG. 3A shows the nucleotide sequence (SEQ ID NO: 17) and deduced amino acid sequence (SEQ ID NO: 18) for mouse GBP, FIG. 3B shows the nucleotide sequence (SEQ ID NO: 19) and deduced amino acid sequence (SEQ ID NO: 20) for human GBP, FIG. 4A shows the effect of natural and recombinant mouse GBP which is monomeric on the growth of mouse embryo fibroblasts (MEF) and the lack of effect, at equivalent dose, of the plant lectins Concanavalin A and succinyl Concanavalin A, FIG. 4B shows mouse embryo fibroblasts after 40 hours growth from seeding, FIG. 4C shows mouse embryo fibroblasts 40 hours from seeding which have been treated with 400 ng ml$^{-1}$ of monomeric GBP, FIG. 4D shows the effect on growth of replicating MEF of the monomeric forms of GBP and of the tetrameric forms of GBP over a period of five days, FIG. 4E shows the DNA distribution as an indicator of cell growth at different stages of the cell cycle in serum stimulated MEF following treatment with GBP, FIG. 5A shows the effect on cell growth of adding a neutralizing antibody to the constitutive endogenous GBP during the G0 phase of the MEF cell cycle, FIG. 5B shows the effect on cell growth when antibody is added prior to the G2 phase of the cell cycle, FIG. 6A shows the effect of murine rGBP on growth of murine transformed cells lines, 18-8, PV-TT-8, Weli 3B and L-57 at varying concentrations, FIG. 6B shows the effect of murine rGBP on growth of human cancer cells, K562, Nalm 6 and KG 1 at varying concentrations, FIG. 7 shows the conversion of non-complexed GBP from monomeric to tetrameric form (left panels) and conversion of completed GBP from monomeric to tetrameric form (right panels) after 6, 12 and 24 hours of incubation at 37° C.

FIG. 8A shows receptor affinity binding of GBP to mouse embryo fibroblasts in the absence of 100 mM competing lactose, FIG. 8B shows receptor affinity binding of GBP to mouse embryo fibroblasts in the presence of 100 mM competing lactose, FIG. 8C compares the affinity of the four forms of GBP, (monomeric and tetrameric), for cell receptors on MEF, and FIG. 9 shows the effect of murine GBP on replication of EMC virus in mouse embryo fibroblasts.

EXAMPLE 1

Isolation of Naturally Occurring Mouse GBP a) Cultures of mouse embryo fibroblasts (MEF) were prepared from mice of the C57 Bl strain.

Primary cells were seeded in Eagle's BHK medium containing 10% tryptose phosphate broth and 10% foetal calf serum (growth medium) in an atmosphere of 5% $CO_2$ in air.

Cells were seeded at a density such that when all cells capable of dividing had undergone one division cycle, a confluent monolayer was obtained.

Cell division occurred at approximately 30 hours after seeding and the cultures were then left for a further 24 hours. These cells were then assessed for plating efficiency and sub-cultured to secondary fibroblasts, using a seed equal to half that expected at confluence. After cell division had occurred (30 hours) the growth medium was changed to BHK medium containing 2% foetal calf serum and the culture maintained in this condition for a further 72 hours.

b) For production of natural GBP secondary HEF were used. Confluent cultures of secondary fibroblasts which had been quiescent in 2% serum for 72 hours were washed three times with phosphate buffered saline (PBS), once with serum free Eagle's BHK medium (SFM) and incubated at 37° C. in SFK (10 ml per $10^7$ cells) for 20 hours. The medium was harvested, centrifuged at 10,000 g for one hour at 4° C. and concentrated in the cold 100 times by volume above a PM10 Amicon ultrafiltration membrane. The total protein concentration of the conditioned medium was measured using the Biorad protein assay with γ-globulin as standard.

c) The conditioned medium (CM) prepared in step (b) was adjusted to have a protein concentration of 1 mg ml$^{-1}$ and applied to Sephadex G 75 columns equilibrated with PBS at 4° C. Elution with PBS was carried out in the cold. Fractions were collected in 10 ml volumes, transferred to dialysis bags and concentrated to 1 ml by withdrawal of water and salts using Ficoll 400. Aliquots of each fraction were assayed for protein concentration, analysed by polyacrylamide gel electrophoresis and tested for growth inhibitory activity. The active fractions were pooled and active protein purified by immunoaffinity chromatography using polyclonal or monoclonal anti-GBP antibodies raised and purified by the inventors as hereinafter described.

d) The cells for assessment of growth inhibitory activity were secondary mouse embryo fibroblasts. Cells were seeded at a concentration of 105 cells cm$^{-2}$ in BHK medium containing 5% foetal calf serum. The cultures were equilibrated with 5% $CO_2$ in air and incubated in a water-bath at 37° C. At chosen times the preparations to be tested for growth inhibitory activity were added. Each of these had previously been dialysed against serum-free medium (SFM) and then supplemented with 5% foetal calf serum. Controls received SFM plus 5% serum. Growth inhibition was measured by removing cells from the glass using 0.5 ml 0.02% ethylene diaminetetra-acetic acid (EDTA) containing 0.1% trypsin plus 0.2% trypan blue. The trypsin was then neutralised with 0.5 ml of serum. Trypan blue stained and unstained cells were counted in a Fuchs-Rosenthal Haemocytometer. In all the experiments the number of stained and therefore non-viable cells was less than 2%.

EXAMPLE 2

Purification by Reverse Phase High Pressure Liquid Chromotography (HPLC) and Characterisation of Mouse GBP a) Reverse phase HPLC of proteins was carried out on pools obtained by G75 Sephadex fractionation of serum-free conditioned medium from G0 C57/Bl secondary MEF as in Example 1. 250 μg of protein was loaded onto a C18 reverse phase HPLC column equilibrated with 0.08% trifluoroacetic acid and a gradient from a 20% to 60% acetonitrile was run over 45 minutes at 1.5 mls min$^{-1}$. Fractions of 0.75 ml were collected. The resulting HPLC trace is shown in FIG. 1A. Two peaks of inhibitory activity were identified (indicated by arrows). When the pooled fractions containing the active peaks of inhibitory activity were run on an SDS gradient polyacrylamide gel the fractions containing the first peak showed a band with an apparent Mr of about 18,000 Daltons. Fractions containing the second peak showed one component migrating with an apparent Mr of about 15,000 Daltons. These bands are clearly shown on the gel in FIG. 1B. It was ascertained by sequence analysis and by the use of monoclonal antibodies that the proteins isolated from the two peaks of inhibitory activity were in fact identical and the difference in molecular weight was attributed to the presence of sugar determinants on the protein of the first peak and in particular to a saccharide complex which binds to the β-galactoside binding site and effectively masks it.

b) 200 μl of the pooled active fractions eluted in the second peak from the reverse phase HPLC column were freeze dried and taken up in 50 μl of sample buffer and run in a single lane of a 12% polyacrylamide slab gel containing 0.1% SDS. The lane was cut into 2 mm slices, each slice eluted into 300 μl of Eagle's BHK medium and shaken overnight on a rotary shaker at 4° C. 200 μl of each recovered supernatant was spun for 15 minutes at 10,000 g at 4° C. 50 μl were run on a 12% SDS polyacrylamide slab gel to be stained with Biorad silver stain. This gel is shown in FIG. 1C. The remaining 150 μl of recovered supernatant were then made to contain 5% foetal bovine serum and 1% fatty acid free bovine serum albumin and added to duplicate cultures of tertiary mouse embryo fibroblasts in multiwell plates. For assessment of growth inhibitory activity cells were fixed in methanol at 40 hours from seeding and stained. The cell number in 5 random fields was counted using an eye piece graticule. FIG. 1C clearly shows a band migrating with the expected Mr which coincides with a sharp peak of cell growth inhibitory activity.

c) Following the purification by virtue of steps (a) and (b) above, amino acid sequence analysis was used for characterisation of the protein at the structural level. Pooled active fractions as shown in FIG. 1A were reduced and alkylated, dialysed against 10 mM ammonium bicarbonate, lyophilised and resuspended in 10 mM ammonium bicarbonate. TPCK treated trypsin was added (100:1, Protein:trypsin, W/W). This mixture was incubated at 37° C. for 12 hours, a further identical aliquot of trypsin added and the incubation continued for a further 12 hours.

Peptides were then loaded directly onto a C18 reverse phase HPLC column equilibrated in 0.08% trifluoroacetic acid.

A gradient from 0 to 60% acetonitrile was run over 75 minutes at 1 ml min$^{-1}$ and 0.5 ml fractions were collected. Sequence determination was carried out on three peptides so produced using an Applied Biosystems 470A gas phase sequencer, PTH amino acid analysis being performed on-line using a 120A analyser.

Quantitative PTH amino acid recovery was measured with a Shimadzu CR3A recording integrator. The three peptide sequences (SEQ ID NOS: 1–3) obtained are shown in FIG. 2A.

A protein database and literature search was performed to identify other proteins showing homology with these three peptide sequences mentioned above. The searches revealed an absolute amino acid identity with sequences of rat lung β-galactoside binding protein, absolute identity, with the exception of one amino acid, with sequences of β-galactoside binding protein from some human tissues and homology with available sequences of other human tissues and tissues from mouse, cow and chicken (SEQ ID NOS: 4–15). This is shown in FIG. 2A where boxed sequences indicate lack of homology. Thus the peptide sequence analysis and subsequent search showed clearly that the MEF inhibitory protein was β-galactoside binding protein. Confirmation that such was the case was made by cloning full length GBP cDNA (as described hereinafter) and comparing the deduced amino acid sequence of mouse GBP with the GBP's of other species as specified in Example 3.

d) Once the full amino acid sequence of GBP (SEQ ID NO: 16) was obtained computer analysis was used to identify the position of any β-galactoside binding sites. FIG. 2Ba shows the amino acid sequence (SEQ ID NO: 16) with the predicted secondary structure indicated and the single saccharide binding site underlined.

FIG. 2Bb is a hydropathic profile of the protein in which the amino acids of the saccharide binding site are in closed symbols. The protein, both natural and recombinant, is expressed in monomeric form (see Example 6). The above analysis clearly demonstrates that the monomeric protein has only a single β-galactoside binding site. This characteristic distinguishes it from the lectins and prevents it from causing cell agglutination.

EXAMPLE 3

Preparation and Isolation of Mouse GBP cDNA from Mouse Embryo Fibroblast cDNA Libraries a) The amino acid sequence of part of one of the peptides shown in FIG. 2A (the sequence that is underlined) was used to deduce a nucleotide sequence for synthesis of four oligonucleotide probes by standard methods known to the skilled man.

b) PolyA$^+$ RNA was isolated from tertiary mouse embryo fibroblasts. Double stranded cDNA was synthesised from this mRNA, ligated into phage λgt 10 DNA and the recombinant phage was packaged in vitro. The λgt 10 cDNA library was then screened in a standard manner with a combination of the four synthetic oligonucleotide probes based on the peptide sequence described previously. A 110 bp cDNA, enclosing the coding region for the amino acid sequence of the peptide used to prepare the oligonucleotide probes, was then isolated and used to screen a CDM8 plasmid library prepared with size fractionated cDNA's (400 to 1200 bp) prepared from mouse fibroblast polyA$^+$ RNA. XhoI cDNA inserts were isolated and selected by size for sequencing by the Sanger dideoxynucleotide termination method. Clone MW2 (SEQ ID NO: 17) was found to consist of 497 nucleotides enclosing an open reading frame of 405 bp with the ATG starting codon in favourable initiation context. Clone MW2 cDNA encodes the amino-terminal methionine and a protein of 134 amino acids with a translated molecular weight of 14,735 Daltons. Flanking the coding region are a 5' untranslated sequence of 19 bp and a 3' untranslated sequence of 73 bp containing a stop codon in position 406, a consensus adenylation signal 23 bp further downstream and a tail of 19 adenosines. The nucleotide sequence for MEF GBP (SEQ ID NO: 17) is shown in FIG. 3A. Comparison with known sequences of rat, human and chicken beta galactoside binding proteins, showed that the GBP's described herein, each consisting of 134 amino acids, showed the following homologies: mouse/rat 96%, mouse/man 89%, mouse/chicken 50%. Hence, especially in the case of mammalian GBP, molecular similarity is very high. This explains the cross-species activity i.e. effect of mouse GBP on human cancer cells as quoted in Example 5.

EXAMPLE 4

Expression of GBP in COS-1 Cells and Purification of the Recombinant Protein a) COS-1 cells which do not naturally express the protein were transfected with a CDM8 plasmid containing the aforementioned clone MW2 at a plasmid cell ratio of 10 μg DNA per 10$^6$ cells using standard methods based on DEAE dextran and DMSO facilitated DNA uptake. The thus expressed recombinant GBP was purified by immunoaffinity chromatography. Although any purification method known to the skilled man might be used at this stage, in this particular example an IgG fraction of a monoclonal antibody (clone B2) raised against the natural MEF GBP was used as an affinity reagent. Because COS-1 cells express both the 15,000 Dalton protein and the glycan-complexed 1,000 Dalton version, (which are also expressed under natural conditions—see FIGS. 1A and 1B), the antibody purified rGBP was subjected to asialofetuin sepharose chromatography. The complexed protein was recovered in the through fraction while the non-complexed protein was recovered by elution from the column by competing sugars.

b) For preparation of a monoclonal antibody to the natural GBP, 8 to 10 week old BALB-C mice were immunised intraperitoneally with GBP purified by electro-elution from a polyacrylamide gel. 50 μg of protein was injected in Freunds' complete adjuvant followed by two injections of 50 μg of protein intraperitoneally in Freunds' incomplete adjuvant at 4 weekly intervals. Immune mice were then boosted by injecting with 50 μg of GBP intravenously and the spleens were removed 3 days later. Spleen cells were fused with NS-1 myeloma cells using polyethylene glycol to induce fusion and were then distributed in selective HAT medium containing 20% foetal calf serum together with spleen cells to form a feeder layer. Once clones had grown to a suitable size, the supernatants were tested for the presence of antibodies to GBP using an ELISA assay. Positive clones were sub-cloned twice by limiting dilution and selected clones were frozen in liquid nitrogen. A clone, B2, was selected for use in the immunoaffinity purification of MEF GBP.

EXAMPLE 5

Growth Inhibitory Activity of Natural and Recombinant GBP a) The growth inhibitory effect of GBP on synchronous mouse embryo fibroblasts (preparation as described hereinbefore) was assessed as described in Example 2. Increasing concentrations of monomeric GBP were tested, as also were increasing parallel concentrations of Concanavalin A and succinyl Concanavalin A for comparison. FIG. 4A shows an equal increase in growth inhibition up to 100% with increasing concentrations (0 to 400 ng ml$^{-1}$) of either natural (●-●), or rGBP, (■-■), while no effect on growth is shown by similar concentrations of Concanavalin A (□-□) or succinyl Con A (Δ-Δ) which, unlike GBP and other physiological growth factors such as interferons whose effect is cell stage specific, require much higher doses and cause non-specific inhibition. FIG. 4B shows a monolayer of control mouse embryo fibroblasts (MEF) and FIG. 4C a monolayer of MEF treated with 400 ng ml$^{-1}$ of monomeric mouse GBP between 4 and 40 hours from the time of seeding. Observations of these cells show that where replication has been impeded, the cells tend to have larger cytoplasm and nuclear areas, or in some cases double nuclei, with cell number not changed from that of the seed.

b) The growth inhibitory effect of monomeric and tetrameric forms of GBP were compared. The existence of tetrameric form of the protein, both complexed with a saccharide and non-complexed was first demonstrated by labelling the protein with $^{125}$I, as described in Example 6. The complexed and non-complexed forms were incubated at 37° C. over a period of 24 hours and then subjected to Sephadex G100 chromatography and estimation of the radioactivity in the fractions. The results are shown in FIG. 7 (left panels non-complexed, right panels complexed) and demonstrate that over the period of 24 hours the monomer can form a tetrameric molecule. However as can be clearly seen from the figures the complexed form resists tetrameric conversion (FIG. 7d, right panel). In the case of tetramers it can be shown that these molecules result from the formation of disulphide bridges because the presence of reducing agents prevent their formation.

The cell growth inhibitory activity of both types of monomers and tetramers was assessed on replicating mouse embryo fibroblasts (preparation as hereinbefore described) at a concentration of 200 ngml$^{-1}$. The results are shown in FIG. 4D and demonstrate that the inhibitory effect of the tetramer (o-o; -□-□-) is weaker than that of the 15,000 Mr monomer 〖-〗 and the 18,000 Mr monomer ▽-▽ which in fact has the most superior growth inhibitory activity. Controls are represented by the symbol o-o. A likely explanation as to why the inhibitory activity of the tetramer is less is that one tetramer can only bind one cell receptor. Furthermore the complexed monomer (18,000 Mr) is the most potent form of the GBP of the invention probably because it resists conversion to the tetrameric form.

d) MEF GBP was tested for its effect on a variety of murine and human cancer cell lines and the results are shown in FIGS. 6A and 6B. Growth of the cell lines incubated with GBP was followed for 3 days and the growth rate compared to an untreated control. A growth inhibitory effect is clearly demonstrated at 100 (Δ-Δ) and 400 (□-□) ng ml$^{-1}$ GBP when applied to 18.8 cells (a pre B cell line), PV-TT-8 cells (polyoma virus-induced sarcoma cells), Weli 3B cells (a myelomonocytic leukaemia cell line) and L-57 (spontaneously transformed mouse fibroblasts), FIG. 6B shows a similar inhibitory effect of GBP when applied to the human cancer cell lines K562 (chronic myelogenous leukaemia), Nalm 6 (acute lymphoblastic leukaemia) and KG 1 (erythroleukaemia). In both FIGS. 6A and 6B controls are shown with the symbols (x-x). In addition to the above GBP was tested on the following the human cell lines myeloblastic haemopoietic cell line HL-60, lymphoblastic B cell line-raji, lymphoblastic T Cell line-MOLT, and lymphoblastic T Cell line -JM at doses ranging from 100 to 250 ngml$^{-1}$ and was seen to cause a decrease of the S and G2 populations and a reduction of growth by 40 to 60%. Thus the mouse GBP, both natural and recombinant, has a powerful inhibitory effect on tumour cells of human origin.

EXAMPLE 6

Characterisation of Mouse GBP and Elucidation of Its Mode of Action a) In order to demonstrate that native GBP was in fact monomeric both the complexed and non-complexed forms, which were separated one from the other by asialofetuin sepharose chromatography, were subjected to SDS gradient gel electrophoresis under both reducing and non-reducing conditions. The result obtained is shown in FIG 1Da in which lanes a', b' and c' were run under reducing conditions and lanes a,b and c under non-reducing conditions. Since reducing agents would have the effect of separating polymeric proteins into monomers which could be detected on the gel, if mouse GBP was anything other than a monomer the position of the band would change where reducing agents were present. As can be seen this was not the case for either the complexed protein (lanes a and a') or the non-complexed protein (lanes c and c'). Lanes b and b' represent a mixture of the two. Thus mouse GBP is clearly demonstrated to be a monomer.

b) It has already been demonstrated in Example 2(d) and particularly shown in FIGS. 2Ba and 2Bb that each monomer has only a single β-galactoside binding site. This permits binding of the non-complexed monomer to an asialofetuin sepharose column. It has further been demonstrated that the complexed form and the tetrameric forms of the protein cannot bind to such a column because they do not have a sugar binding site available.

In the case of the complexed protein, either monomeric or tetrameric, the saccharide binding site is masked by a saccharide complex.

In the case of the tetramer from the non-complexed form the saccharide binding site on each component monomer is internal and therefore not available for binding.

It was first demonstrated that the 18,000 Mr protein was associated with a saccharide complex by blotting onto nitrocellulose the 18,000 Mr and 15,000 Mr forms of GBP, the glycosylated protein transferrin and the non-glycosylated N-terminus fragment of transferrin as controls and by using an ELIZA Glycan Detection Kit (Boehringer Mannheim Biochemica) used to detect proteins containing sugar complexes. The result is shown in FIG. 1Db in which lane (a) is 18,000 Mr GBP, lane (b) is 15,000 Mr GBP, lane (c) is transferrin and lane (d) is the N-terminus fragment of transferrin. The concentrations of protein are from left to right 120 ng, 60 ng and 30 ng respectively.

The high degree of staining of lanes a and c indicates the presence sugar complexes. Thus the 18,000 Mr protein displays such complexes which are clearly absent in the 15,000 Mr protein.

The nature of the binding of the glycan complex was further investigated to see whether there was 0-glycosylation of the protein or whether the glycan complex was linked to the protein by some other means.

The recombinant complexed protein was separated from the non-complexed protein using asialofetuin sepharose chromatography where the non-complexed protein was retained, as described before. The complexed protein was then subjected to SDS polyacrylamide gel electrophoresis after enzyme treatments with 0-deglycosylating enzyme in the presence and absence of lactose and/or neuraminidase. The results are shown in FIG. 1E in which the treatments are as follows:

| | |
|---|---|
| a | 18,000 GBP control |
| b | 18,000 GBP + lactose |
| c | 18,000 GBP + 0-deglycosylating enzyme |
| d | 18,000 GBP + 0-deglycosylating enzyme + lactose |
| e | 18,000 GBP + 0-deglycosylating enzyme + neuraminidase + lactose |
| f | 18,000 GBP + 0-deglycosylating enzyme + neuraminidase |
| g | 18,000 GBP + neuraminidase + lactose |
| h | 18,000 GBP + neuraminidase |
| i | 15,000 GBP control |

The experiment of FIG. 1E demonstrates that the saccharide complex, which contains sialic acid residues, did not originate from an 0-glycosylation site of the molecule as it could not be removed by the deglycosylating enzyme, but that it could be removed by competition with lactose once the sialic acid residues of the saccharide complex had been removed by digestion with neuraminidase.

c) It has been demonstrated by the experiments described in (b) above that in the complexed GBP the β-galactoside binding site is masked by a saccharide complex. It has also been demonstrated that the tetrameric forms of the protein do not have an available sugar binding site because of its inability to bind to an asialofetuin sepharose column. Nevertheless these forms of GBP have demonstrable cell growth inhibitory activity which indicates that the growth inhibitory effect is not associated with the sugar binding capacity of the protein.

In order to demonstrate that the sugar binding site is not involved in the growth inhibitory effect, even in the case where it is not masked, affinity binding of GBP to specific cell surface receptors on mouse embryo fibroblasts was assayed in the presence or absence of a competing sugar (FIGS. 8A and 8B). Binding assays were carried out also to compare the affinity of each of the four forms of GBP (monomeric, complexed and non-complexed and tetrameric, completed and non-complexed) for the cell receptors of mouse embryo fibroblasts (FIG. 8C).

Binding assays were undertaken using GBP labelled with $^{125}$I. The protein was radio-iodinated by mixing 1 µg with 500 µCi of carrier free Na $^{125}$I in 100 µl of 100 m! NaPi, pH 7 using preloaded iodo-bead iodination reagent. After stopping the reaction, 300 µl of 100 mM NaPi with 0.1% BSA was added and the iodinated protein separated on a Biorad DG10 column equilibrated with 0.1% BSA in 100 mM NaPi. The specific activity ranged from $4 \times 10^5$ to $8 \times 10^5$ cpm µg$^{-1}$. Samples were checked by polyacrylamide gel electrophoresis and tested for biological activity before the binding assays were carried out. Competition binding assays were carried out at 4° C. on triplicate mouse embryo fibroblast cultures in Falcon 24 well Multiwell plates. The cells ($2 \times 10^5$ per well) which had been pre-refrigerated and washed three times with cold binding buffer (PBS with Ca++ and Mg++ plus 0.1% BSA) received 0.625 ng of $^{125}$I-labelled GBP premixed with increasing concentrations of un-labelled GBP. Equilibrium binding was reached at 3 hours and after 4 hours the cells were washed three times with cold binding buffer and solubilised in 0.1 mM NaOH, 2% $Na_2 CO_3$ and 1% SDS. The assay was first carried out with and without the presence of 100 mM lactose as a competing sugar. Where competing lactose was added this was pre-incubated for 20 minutes at room temperature with the GBP solutions. The results of this experiment are shown in FIGS. 8A & 8B in which 8A demonstrates the affinity binding of GBP to mouse embryo fibroblasts in the absence of lactose and FIG. 8B demonstrates binding in the presence of lactose. The inserts are Scatchard plots showing that in either condition the protein binds to an estimated $5-10 \times 10^4$ specific receptors with very high affinity and that binding must therefore occur through a domain other than that which binds saccharides. It is clear from the results of these binding assays that the lactose is not in any way impeding binding on to cells and that therefore the sugar binding site cannot be involved in the growth inhibitory effect of the molecule as already obvious for the complexed and the tetrameric forms. In accord with the binding experiments cells treated with GBP, whether or not in the presence of a competing sugar, did not proceed into growth while sugar alone had no effect.

Further receptor binding assays were then carried out using the four different forms of GBP. The results are shown in FIG. 8C in which (a) is GBP 15,000 (b) is GBP 18,000, (c) is tetramer of GBP 15,000 and (d) is tetramer of GBP 18,000. It is clear from the results that binding of 125 I labelled protein was blocked with similar modalities by the same excess of labelled protein in all instances and that the estimated number of binding sites per cell and the relative Kds give similar values (scatchard plots, insets). Thus the efficiency of cell receptor binding is the same for all four forms of the protein.

EXAMPLE 7

Studies of the Mode of Action of MEF GBP on the Cell Cycle a) To investigate the modalities of cell growth inhibition, cell cycle analysis was performed by cytofluorimetic quantitation of DNA content of quiescent and serum stimulated mouse embryo fibroblasts treated with 400 ng ml$^{-1}$ of monomeric GBP. The results of this analysis are shown in FIG. 4E in which (a) represents quiescent G0 cells, (b) represents cells stimulated by addition of 10% foetal calf serum, (c) represents serum stimulated ells pretreated during G0 from 4 hours prior to serum stimulation, (d) represents cells treated from the beginning of G1 (3 h after serum stimulation) and (e) cells treated from 4 hours prior to G2.

It was found from these cell cycle studies that when untreated control cells (4E*b*) were traversing G2, cells treated with GBP in G0 remained held in G0 (4E*c*). The cells treated in G0 had not divided by the time the control cells had completed their cycle. Further experiments (not shown) showed that a similar effect was achievable with concentrations of GBP lower than 50 ng ml$^{-1}$. Thus GBP can inhibit cell proliferation by blocking cells in G0.

When GBP was added during G1 (FIG. 4E*d*) progress to the S phase of the cell cycle was not inhibited but instead the transition from late S phase through G2 was affected.

Traverse from late S phase through G2 was also affected when GBP was added prior to the cells entering G2 (FIG. 4E*e*). The cells did not divide by the time control cells had replicated. Again further experiments (not shown) showed that cell growth was delayed for several hours with doses as low as 10 ng ml$^{-1}$. It is envisaged that in a different experimental system even lower doses would be effective.

Concanavalin A and succinyl Concanavalin A were also tested in these cell cycle experiments at the same dose and shown to have no effect.

b) The regulatory role of the constitutive, endogenous GBP was further investigated by examining the effect of a neutralizing monoclonal antibody to mouse GBP on the endogenous protein. Monoclonal antibodies were raised to GBP which was purified by HPLC and eluted from a sliced gel. Eliza positive clones from Balb/C-NS-1 myeloma hybrids were subcloned twice and the IgG fraction from clone B2 was purified using rabbit anti-mouse IgG.

The neutralizing antibody was first added to mouse embryo fibroblasts in the G0 phase. In FIG. 5A, (a) represents quiescent (G0) cells, (b) represents serum stimulated control cells and (c) represents cells treated from 6 hours prior to serum stimulation. In a second experiment, the results of which are shown in FIG. 5B, neutralizing antibody was added prior to the entry into G2 phase. In this case the cells were (a) quiescent (G0) cells, (b) serum stimulated control cells and (c) cells treated from 6 hours prior to G2. In both experiments the amount of neutralizing antibody added was 0.5 µg ml$^{-1}$.

From the results shown in FIG. 5A it can be seen that cells treated previous to serum stimulation (c) traversed S and G2 some 2 hours earlier than controls (b). This indicates that in mouse cells constitutive GBP has a role in maintaining cells in the stationary state. The results in FIG. 5B show that in cells exposed to antibodies previous to entry into G2, progress through S and G2 was faster (c) than in the untreated cells (b), indicating a role also in the control of this period of the cell cycle.

The experiments of Example 7 show that GBP inhibits cell proliferation with cell stage specificity as in the case for interferons which operate in G0 and in G1, and that its effect is therefore that of a cytokine and not that of a lectin.

EXAMPLE 8

Studies on Effect of GBP or Viral Replication

Murine rGBP was tested for its anti-viral activity against the RNA virus enchephalonyocarditis virus (EMC). Mouse embryo fibroblasts were infected with EMC virus at 10 plaque forming units per cell and GBP added after virus absorption. The extent of viral replication was measured by incorporation of $^3$H-uridine into the viral RNA after treatment of the MEF with actinomycin D to halt the host cell RNA production. The infected cells were treated with 200, 20 and 2 ng ml$^{-1}$ GBP and the level of viral replication compared with controls. The results are shown in FIG. 9 and clearly demonstrate that, even at a concentration as low as 2 ng ml$^{-1}$ GBP causes a significant reduction in the replication of the virus.

Accordingly GBP's as defined herein have potential use also as anti-viral agents.

EXAMPLE 9 cDNA for Human GBP

The cDNA for a human non-agglutinating β-galactoside binding protein which is monovalent with respect to sugar binding (human GBP) has also been cloned by the inventors in bacteriophage λgt 11. The nucleotide sequence (SEQ ID NO: 19) and the deduced amino acid sequence (SEQ ID NO: 20) (134 amino acids M.W. 14,744) is shown in FIG. 3B. Given the clearly demonstrated growth inhibitory effect of the mouse GBP on human malignant cells, which would not have been expected from prior knowledge, it is reasonable to assume that the equivalent human protein will have an even more powerful growth inhibitory effect on human malignant cells.

This newly discovered inhibitory activity of animal β-galactoside binding proteins means that they possess enormous potential as therapeutic agents in malignant disease. Further a regulatory effect is to be expected on cells of the immune system and thus a therapeutic use in autoimmune diseases is also envisaged.

In addition, it has further been demonstrated by the inventors that the proteins of this class also have an inhibitory effect on viral replication, thus providing another potential therapeutic use.

The isolation and purification of a naturally occurring non-agglutinating mouse GBP, its production by recombinant DNA technology and its powerful inhibitory effect on growth of mouse and human transformed cells and on viral replication has been given merely by way of example of the potential use of these non-agglutinating animal GBP's generally, and in particular, the potential use of a GBP of human origin. Given the knowledge that these animal GBP's can possess this powerful growth inhibitory effect it is within the ordinary abilities of the skilled man to produce other GBP's having therapeutic use by this route.

We claim:

1. An isolated substantially pure non-agglutinating β-galactoside binding protein which is capable of inhibiting the growth of vertebrate cells, said protein being a monomer that is free of the dimeric form and that comprises an amino acid sequence selected from the group consisting of:
   (a) the amino acid sequence of SEQ ID NO: 18;
   (b) the amino acid sequence of SEQ ID NO: 20;
   (c) an amino acid sequence consisting of amino acids 2 to 135 of SEQ ID NO: 18 or SEQ ID NO: 20; and
   (d) an amino acid sequence which differs from the amino acid sequence of (a), (b) or (c) by having one or more amino acid residues from the region of amino acid position 63 to amino acid position 76 substituted by a different amino acid.

2. A non-agglutinating β-galactoside binding protein according to claim 1 which is obtained by expression of its encoding DNA in a host cell and recovery of the protein from the host cell, said encoding DNA being comprised in a recombinant vector.

3. A non-agglutinating β-galactoside binding protein according to claim 1 for use as a therapeutic agent in the treatment of malignant tumors or as an anti-viral agent.

4. A protein according to claim 1, which is of human origin.

5. A protein according to claim 1 which is of murine origin.

6. A tetrameric protein comprising four identical monomers according to claim 1.

7. A protein according to claim 1 in which the βgalactoside binding site is masked.

8. A protein according to claim 7 in which the β-galactoside binding site is masked by a saccharide complex.

9. A protein according to claim 8 in which the saccharide complex contains sialic acid.

10. A method of inhibiting the growth of vertebrate cells comprising applying to said cells a non-agglutinating β-galactoside binding protein according to claim 1.

11. A method according to claim 10 wherein the vertebrate cells are transformed cells.

12. A method according to claim 11 wherein the transformed cells are of human origin.

13. A method according to claim 11 or 12 wherein the transformed cells are cancer cells.

14. A method of regulating and controlling the growth and replication of vertebrate cells comprising applying to said cells a non-agglutinating β-galactoside binding protein according to claim 1.

15. A pharmaceutical composition comprising the protein of claim 1 together with a carrier or diluent, said protein being present in an amount effective to inhibit the growth of vertebrate cells when contacted therewith.

16. A pharmaceutical composition according to claim 15 wherein when in unit dosage form each unit dose contains from 10 ng to 1000 mg of said protein.

17. A non-agglutinating β-galactoside binding protein according to claim 1, wherein at least one of the amino acids from amino acid position 63 to amino acid position 76 is glycosylated.

18. An isolated substantially pure non-agglutinating β-galactoside binding protein which is capable of inhibiting the growth of vertebrate cells, said protein being a tetramer which comprises four identical monomers of claim 1.

19. A method of treating a disease associated with the presence of malignant tumor cells, said method comprising applying to said malignant tumor cells the non-agglutinating β-galactoside binding protein of claim 1 in an amount sufficient to inhibit the growth of said malignant cells.

20. A plasmid containing the full-length cDNA comprising the nucleic acid sequence as set forth in SEQ ID NO: 17.

* * * * *